(12) United States Patent
Weston et al.

(10) Patent No.: US 10,493,182 B2
(45) Date of Patent: Dec. 3, 2019

(54) SUSTAINED VARIABLE NEGATIVE PRESSURE WOUND TREATMENT AND METHOD OF CONTROLLING SAME

(71) Applicants: Smith & Nephew, Inc., Memphis, TN (US); Smith & Nephew PLC, Watford, Hertfordshire (GB)

(72) Inventors: Richard Scott Weston, Carlsbad, CA (US); Edward Yerbury Hartwell, York (GB)

(73) Assignees: Smith & Nephew, Inc., Memphis, TN (US); Smith & Nephew PLC, Watford (GB)

( * ) Notice: Subject to any disclaimer, the term of this patent is extended or adjusted under 35 U.S.C. 154(b) by 13 days.

(21) Appl. No.: 16/009,699

(22) Filed: Jun. 15, 2018

(65) Prior Publication Data
US 2019/0001032 A1    Jan. 3, 2019

Related U.S. Application Data

(63) Continuation of application No. 14/945,935, filed on Nov. 19, 2015, now Pat. No. 9,999,711, which is a
(Continued)

(51) Int. Cl.
*A61M 1/00* (2006.01)
*A61M 27/00* (2006.01)

(52) U.S. Cl.
CPC ........ *A61M 1/0037* (2013.01); *A61M 1/0027* (2014.02); *A61M 1/0031* (2013.01);
(Continued)

(58) Field of Classification Search
CPC .. A61M 1/0025; A61M 1/0029; A61M 27/00; A61M 2230/205; A61M 1/0027;
(Continued)

(56) References Cited

U.S. PATENT DOCUMENTS

| 1,480,562 A | 1/1924 | Mock |
| 3,171,410 A | 3/1965 | Towle, Jr. et al. |

(Continued)

FOREIGN PATENT DOCUMENTS

| DE | 1963258 | 6/1971 |
| DE | 4 012 232 A1 | 10/1991 |

(Continued)

OTHER PUBLICATIONS

U.S. Appl. No. 12/192,000, filed Apr. 14, 2008, Hartwell et al.
Australian Office Action for corresponding Australian Application No. 2009204140, dated Feb. 15, 2013, in 3 pages.
Japanese Office Action for corresponding Japanese Application No. 2010-542353, dated Mar. 26, 2013, in 8 pages.
(Continued)

*Primary Examiner* — Joshua Lee
(74) *Attorney, Agent, or Firm* — Knobbe, Martens, Olson & Bear, LLP

(57) ABSTRACT

Disclosed herein are systems and methods for providing reduced or negative pressure, and more particularly cyclical reduced pressure, to treat a wound. The system can include a wound dressing, a fluid collection container, a suction source, filters, and conduits. In addition, the system can include a control device and sensors. The sensors may be configured to monitor certain physiological conditions of a patient such as temperature, pressure, blood flow, blood oxygen saturation, pulse, cardiac cycle, and the like. Application of cyclical reduced pressure between two or more values below atmospheric pressure may be synchronized with the physiological conditions monitored by the sensors. Certain embodiments of the system utilize an air reservoir and one or more valves and pressure sensors or gauges to allow for rapid cycling of the level of reduced pressure within the wound dressing between two or more reduced pressure values.

11 Claims, 11 Drawing Sheets

Related U.S. Application Data continuation of application No. 13/758,209, filed on Feb. 4, 2013, now Pat. No. 9,192,700, which is a continuation of application No. 12/812,232, filed as application No. PCT/US2009/030497 on Jan. 8, 2009, now Pat. No. 8,366,692.

(60) Provisional application No. 61/019,819, filed on Jan. 8, 2008.

(52) U.S. Cl.
CPC .......... *A61M 1/0088* (2013.01); *A61M 27/00* (2013.01); *A61M 2205/18* (2013.01); *A61M 2230/00* (2013.01); *A61M 2230/005* (2013.01); *A61M 2230/04* (2013.01); *A61M 2230/205* (2013.01); *A61M 2230/50* (2013.01)

(58) Field of Classification Search
CPC .............. A61M 1/0031; A61M 1/0037; A61M 1/0088; A61M 2230/00; A61M 2230/04; A61M 2230/50
See application file for complete search history.

(56) References Cited

U.S. PATENT DOCUMENTS

| | | |
|---|---|---|
| 3,633,567 A | 1/1972 | Sarnoff |
| 3,874,387 A | 4/1975 | Barbieri |
| 3,993,080 A | 11/1976 | Loseff |
| 4,112,947 A | 9/1978 | Nehring |
| 4,136,696 A | 1/1979 | Nehring |
| 4,184,510 A | 1/1980 | Murry et al. |
| 4,224,945 A | 9/1980 | Cohen |
| 4,316,466 A | 2/1982 | Babb |
| 4,382,441 A | 5/1983 | Svedman |
| 4,465,485 A | 8/1984 | Kashmer et al. |
| 4,573,965 A | 3/1986 | Russo |
| 4,710,165 A | 12/1987 | McNeil et al. |
| 4,740,202 A | 4/1988 | Stacey et al. |
| 4,772,259 A | 9/1988 | Frech et al. |
| 4,778,446 A | 10/1988 | Jensen |
| 4,792,328 A | 12/1988 | Beck et al. |
| 4,921,488 A | 5/1990 | Maitz et al. |
| 4,936,834 A | 6/1990 | Beck et al. |
| 4,969,880 A | 11/1990 | Zamierowski |
| 5,000,164 A | 3/1991 | Cooper |
| 5,055,198 A | 10/1991 | Shettigar |
| 5,073,172 A | 12/1991 | Fell |
| 5,100,396 A | 3/1992 | Zamierowski |
| 5,176,663 A | 1/1993 | Svedman et al. |
| 5,184,077 A | 2/1993 | Day et al. |
| 5,261,893 A | 11/1993 | Zamierowski |
| 5,328,614 A | 7/1994 | Matsumura |
| 5,358,494 A | 10/1994 | Svedman |
| 5,380,280 A | 1/1995 | Peterson |
| 5,419,768 A | 5/1995 | Kayser |
| 5,429,601 A | 7/1995 | Conley et al. |
| 5,449,347 A | 9/1995 | Preen et al. |
| 5,498,338 A | 3/1996 | Kruger et al. |
| 5,548,562 A | 8/1996 | Helgerud et al. |
| 5,549,584 A | 8/1996 | Gross |
| 5,636,643 A | 6/1997 | Argenta |
| 5,645,081 A | 7/1997 | Argenta et al. |
| 5,759,570 A | 6/1998 | Arnold |
| 6,135,116 A | 10/2000 | Vogel et al. |
| 6,142,982 A | 11/2000 | Hunt |
| 6,159,160 A | 12/2000 | Hsei et al. |
| 6,254,567 B1 | 7/2001 | Treu et al. |
| 6,398,767 B1 | 6/2002 | Fleischmann |
| 6,458,109 B1 | 10/2002 | Henley et al. |
| 6,465,708 B1 | 10/2002 | Augustine |
| 6,547,756 B1 | 4/2003 | Greter et al. |
| 6,626,827 B1 | 9/2003 | Felix et al. |
| 6,685,681 B2 | 2/2004 | Lockwood et al. |
| 6,695,824 B2 | 2/2004 | Howard et al. |
| 6,752,794 B2 | 6/2004 | Lockwood et al. |
| 6,755,807 B2 | 6/2004 | Risk et al. |
| 6,856,821 B2 | 2/2005 | Johnson |
| 6,979,324 B2 | 12/2005 | Bybordi et al. |
| 6,994,702 B1 | 2/2006 | Johnson |
| 7,004,915 B2 | 2/2006 | Boynton et al. |
| 7,022,113 B2 | 4/2006 | Lockwood et al. |
| 7,077,832 B2 | 7/2006 | Fleischmann |
| 7,108,683 B2 | 9/2006 | Zamierowski |
| 7,128,735 B2 | 10/2006 | Weston |
| 7,195,624 B2 | 3/2007 | Lockwood |
| 7,214,202 B1 | 5/2007 | Vogel et al. |
| 7,216,651 B2 | 5/2007 | Argenta et al. |
| 7,276,051 B1 | 10/2007 | Henley et al. |
| 7,361,184 B2 | 4/2008 | Joshi |
| 7,494,482 B2 | 2/2009 | Orgill et al. |
| 7,524,315 B2 | 4/2009 | Blott et al. |
| 7,534,927 B2 | 5/2009 | Lockwood et al. |
| 7,611,500 B1 | 11/2009 | Lina et al. |
| 7,615,036 B2 | 11/2009 | Joshi et al. |
| 7,648,488 B2 | 1/2010 | Smith et al. |
| 7,699,830 B2 | 4/2010 | Martin |
| 7,708,724 B2 | 5/2010 | Weston |
| 7,731,702 B2 | 6/2010 | Byordi |
| 7,753,894 B2 | 7/2010 | Blott et al. |
| 7,776,028 B2 | 8/2010 | Miller et al. |
| 7,779,625 B2 | 8/2010 | Joshi et al. |
| 7,790,945 B1 | 9/2010 | Watson, Jr. |
| 7,794,450 B2 | 9/2010 | Blott et al. |
| 7,811,269 B2 | 10/2010 | Boynton et al. |
| 7,846,141 B2 | 12/2010 | Weston |
| 7,883,494 B2 | 2/2011 | Martin |
| 7,909,805 B2 | 3/2011 | Weston |
| 7,964,766 B2 | 6/2011 | Blott et al. |
| 7,998,125 B2 | 8/2011 | Weston |
| 8,007,257 B2 | 8/2011 | Heaton et al. |
| 8,062,272 B2 | 11/2011 | Weston |
| 8,100,887 B2 | 1/2012 | Weston |
| 8,105,295 B2 | 1/2012 | Blott et al. |
| 8,162,909 B2 | 4/2012 | Blott et al. |
| 8,197,467 B2 | 6/2012 | Heaton et al. |
| 8,235,955 B2 | 8/2012 | Blott et al. |
| 8,257,327 B2 | 9/2012 | Blott et al. |
| 8,308,714 B2 | 11/2012 | Weston et al. |
| 8,338,402 B2 | 12/2012 | Fry et al. |
| 8,348,910 B2 | 1/2013 | Blott et al. |
| 8,366,692 B2 | 2/2013 | Weston et al. |
| 8,398,614 B2 | 3/2013 | Blott et al. |
| 8,480,641 B2 | 7/2013 | Jacobs |
| 8,641,691 B2 | 2/2014 | Fink et al. |
| 8,784,393 B2 | 7/2014 | Weston et al. |
| 8,852,149 B2 | 10/2014 | Weston et al. |
| 8,974,429 B2 | 3/2015 | Gordon et al. |
| 9,044,579 B2 | 6/2015 | Blott et al. |
| 9,192,700 B2 | 11/2015 | Weston et al. |
| 9,386,947 B2 | 7/2016 | Johnson |
| 9,999,711 B2 | 6/2018 | Weston et al. |
| 2001/0034499 A1 | 10/2001 | Sessions et al. |
| 2002/0082544 A1 | 6/2002 | Thrash et al. |
| 2002/0115952 A1 | 8/2002 | Johnson |
| 2002/0161346 A1 | 10/2002 | Lockwood et al. |
| 2002/0183659 A1 | 12/2002 | Krause |
| 2002/0198474 A1 | 12/2002 | Becker |
| 2003/0021775 A1 | 1/2003 | Freeman |
| 2003/0033032 A1 | 2/2003 | Lind et al. |
| 2003/0040687 A1 | 2/2003 | Boynton et al. |
| 2003/0144619 A1 | 7/2003 | Augustine |
| 2003/0171675 A1 | 9/2003 | Rosenberg |
| 2003/0212357 A1 | 11/2003 | Pace |
| 2003/0216672 A1 | 11/2003 | Rastegar et al. |
| 2004/0064132 A1 | 4/2004 | Boehringer et al. |
| 2004/0073151 A1* | 4/2004 | Weston ............... A61F 15/008 602/41 |
| 2004/0122434 A1 | 6/2004 | Argenta et al. |
| 2004/0127845 A1 | 7/2004 | Renz et al. |
| 2004/0230132 A1 | 11/2004 | Shehada |
| 2005/0065484 A1 | 3/2005 | Watson, Jr. |
| 2006/0149171 A1 | 7/2006 | Vogel |

(56) References Cited

U.S. PATENT DOCUMENTS

| | | | |
|---|---|---|---|
| 2006/0173253 | A1 | 8/2006 | Ganapathy et al. |
| 2006/0213527 | A1 | 9/2006 | Argenta |
| 2007/0014837 | A1 | 1/2007 | Johnson et al. |
| 2007/0021697 | A1 | 1/2007 | Ginther et al. |
| 2007/0038172 | A1 | 2/2007 | Zamierowski |
| 2007/0066945 | A1 | 3/2007 | Martin |
| 2007/0118096 | A1 | 5/2007 | Smith et al. |
| 2007/0129660 | A1 | 6/2007 | McLeod et al. |
| 2007/0219497 | A1 | 9/2007 | Blott et al. |
| 2007/0293830 | A1 | 12/2007 | Martin |
| 2007/0299412 | A1 | 12/2007 | Vogel |
| 2008/0033324 | A1 | 2/2008 | Cornet |
| 2008/0041401 | A1 | 2/2008 | Casola |
| 2008/0200906 | A1 | 8/2008 | Sanders et al. |
| 2008/0208147 | A1 | 8/2008 | Argenta et al. |
| 2008/0234641 | A1 | 9/2008 | Locke et al. |
| 2009/0030402 | A1 | 1/2009 | Adahan |
| 2009/0043268 | A1 | 2/2009 | Eddy et al. |
| 2009/0054855 | A1 | 2/2009 | Blott et al. |
| 2009/0105671 | A1 | 4/2009 | Daggar et al. |
| 2009/0143753 | A1 | 6/2009 | Blott et al. |
| 2009/0157016 | A1 | 6/2009 | Adahan |
| 2009/0221977 | A1 | 9/2009 | Blott et al. |
| 2009/0312723 | A1 | 12/2009 | Blott et al. |
| 2010/0022990 | A1 | 1/2010 | Karpowicz et al. |
| 2010/0036367 | A1 | 2/2010 | Krohn |
| 2010/0057025 | A1 | 3/2010 | Aicher |
| 2010/0063483 | A1 | 3/2010 | Adahan |
| 2010/0100075 | A1 | 4/2010 | Weston et al. |
| 2010/0211030 | A1 | 8/2010 | Turner et al. |
| 2010/0249733 | A9 | 9/2010 | Blott et al. |
| 2011/0004171 | A1 | 1/2011 | Blott et al. |
| 2011/0251569 | A1 | 10/2011 | Turner et al. |
| 2012/0001762 | A1 | 1/2012 | Turner et al. |
| 2016/0038064 | A1 | 2/2016 | Johnson |

FOREIGN PATENT DOCUMENTS

| | | |
|---|---|---|
| DE | 198 44 355 | 4/2000 |
| EP | 0 020 662 B1 | 7/1984 |
| EP | 0 880 953 B1 | 5/1998 |
| FR | 1 163 907 | 5/1958 |
| GB | 114754 | 4/1918 |
| GB | 641061 | 8/1950 |
| GB | 1224009 A | 3/1971 |
| GB | 1549756 A | 8/1979 |
| GB | 2195255 A | 4/1988 |
| GB | 2235821 | 3/1991 |
| GB | 2378392 A | 2/2003 |
| SU | 1251912 A1 | 8/1986 |
| WO | WO 1984/01904 | 5/1984 |
| WO | WO 1991/00718 | 1/1991 |
| WO | WO 1991/16030 | 10/1991 |
| WO | WO 1992/20299 | 11/1992 |
| WO | WO 1996/05873 | 2/1996 |
| WO | WO 2000/07653 | 2/2000 |
| WO | WO 2000/21586 | 4/2000 |
| WO | WO 2000/50143 | 8/2000 |
| WO | WO 2001/024709 | 4/2001 |
| WO | WO 2002/083046 | 10/2002 |
| WO | WO 2004/037334 | 5/2004 |
| WO | WO 2005/105174 | 11/2005 |
| WO | WO 2006/014764 | 2/2006 |
| WO | WO 2006/114637 | 11/2006 |
| WO | WO 2007/019038 | 2/2007 |
| WO | WO 2007/031757 | 3/2007 |
| WO | WO 2007/087809 | 8/2007 |
| WO | WO 2008/010094 | 1/2008 |
| WO | WO 2008/027449 | 3/2008 |
| WO | WO 2008/086397 | 7/2008 |
| WO | WO 2008/143628 | 11/2008 |
| WO | WO 2009/114624 | 9/2009 |

OTHER PUBLICATIONS

Japanese Office Action for corresponding Japanese Application No. 2010-542353, dated Jan. 7, 2014, in 8 pages.

International Search Report and Written Opinion, re PCT Application No. PCT/US2009/030497, dated Sep. 28, 2009.

Written Opinion of the International Secondary Authority, re PCT Application No. PCT/US2009/030497, dated Sep. 28, 2009, in 12 pages.

International Preliminary Report on Patentability, re PCT Application No. PCT/GB2005/001577, dated Nov. 1, 2006.

International Search Report, re PCT Application No. PCT/GB2005/001577, dated Aug. 31, 2005.

Arnljots, B. et al., "Irrigation Treatment in Split-Thickness Skin Grafting of Intractable Leg Ulcers," Scandinavian Journal of Plastic and Reconstructive Surgery, 1985, vol. 19, pp. 211-213, in 3 pages.

Aubrey, D.A. et al., "Treatment of the Perineal Wound after Proctectomy by Intermittent Irrigation", Arch. Surg., Oct. 1984, vol. 119, pp. 1141-1144, in 4 pages.

Bagautdinov, "Variant of External Vacuum Aspiration in the Treatment of Purulent Diseases of Soft Tissues," Current Problems in Modern Clinical Surgery, 1986, 4 pages.

Chariker, M.E. et al, "Effective Management of Incisional and Cutaneous Fistulae with Closed Suction Wound Drainage," Contemporary Surgery. Jun. 1989, pp. 59-63, vol. 34 USA.

Dilmaghani, A. et al., "A Method for Closed Irrigation and Suction Therapy in Deep Wound Infections," Journal of Bone and Joint Surgery, 1969, vol. 51-A, No. 2, pp. 323-342, in 20 pages.

Fleck, C.A., "When Negative is Positive: A Review of Negative Pressure Wound therapy", Wound Care, Mar./Apr. 2004, pp. 20-25, in 6 pages.

Froberg, Birgitta et al., Vacusac Therapy—A Supplement to the Treatment of Varicose Ulcers? (Stockholm) 1990, in 37 pages.

Gupta, S., Ed., "Guidelines for Managing Pressure Ulcers with Negative Pressure Wound Therapy", Advances in Skin & Wound Care Suppl., Nov./Dec. 2004, vol. 17(2), pp. 1-16, in 16 pages.

Hartz, R.S. et al., "Healing of the Perineal Wound", Arch. Surg., Apr. 1980, vol. 115, pp. 471-474, in 4 pages.

Jeter, K. et al., "Managing Draining Wounds and Fistulae: New and Established Methods", Chronic Wound Care, Chapter 27, pp. 240-246, 1990, in 7 pages.

Kloth, L.C. et al., "Chapter 10—Adjunctive Interventions for Wound Healing", Wound Healing Alternatives in Management, 3rd Ed., 2002, pp. 339-352, in 15 pages.

Landis, E.M. et al., "The Effects of Alternate Suction and Pressure on Blood Flow to the Lower Extremities", Alternate Suction and Pressure, J Clin Invest. Sep. 1933, vol. 12(5), pp. 925-961.

Mendez-Eastman, S., Guidelines for Using Negative Pressure Wound Therapy, Advances in Skin & Wound Care, 14(6), Nov./Dec. 2001, 314-325.

Meyer, W. & Schmieden, V., Bier's Hyperemic Treatment, W B. Saunders Company 1908, (the entire reference has been submitted, but pp. 44-65 may be the most relevant).

Morykwas, M. J., et al., "Vacuum-Assisted Closure: A New Method for Wound Control and Treatment: Animal Studies and Basic Foundation," *Annals of Plastic Surgery* 38 (1997) 553-562, Dec. 10, 1996.

Morykwas, M.J., et al., Effects of Varying Levels of Subatmospheric Pressure on the Rate of Granulation Tissue Formation in Experimental Wounds in Swine, Abs., Ann. Plast. Surg. 2001, 47: 547.

NURSING75, "Wound Suction: Better Drainage with Fewer Problems", Nursing, vol. 5, No. 10, Oct. 1975, pp. 52-55.

Svedman, "Irrigation Treatment of Leg Ulcers," The Lancet, Sep. 3, 1983, pp. 532-534.

Svedman, P., A Dressing Allowing Continuous Treatment of a Biosurface, IRCS Med. Science: Biomed. Tech.; Clinic. Med.; Surg. and Transplantation, 1979, 7, p. 221.

Svedman, P., et al., "A Dressing System Providing Fluid Supply and Suction Drainage Used for Continuous or Intermittent irrigation," Annals of Plastic Surgery, vol. 17, No. 2, Aug. 1986, pp. 125-133.

Swift, et al, Quorum Sensing in Aeromonas hydrophila and Aeromonas salmonicida: Identification of LuxR1 Homologs AhyRI and AsaRI and Their Cognate N-Acylhomoserine Lactone Signal Molecules, J. Bacteriol., 1997, 179(17):5271-5281.

(56) References Cited

OTHER PUBLICATIONS

Teder, H. et al., "Continuous Wound Irrigation in the Pig," Journal of Investigative Surgery, 1990, vol. 3, pp. 399-407, in 9 pages.
Tittel, K. et al., "Forum: VariDyne—Neue Standards in der Postoperative Wunddrainage" (New Standards in Postoperative Wound Drainage), Unfallchirurgie, 1988, vol. 14(2), pp. 104-107 (in German with English Translation), in 6 pages.
Tribble, D., "An Improved Sump Drain-Irrigation Device of Simple Construction", Archives of Surgery New York, pp. 511-513, 1972, vol. 105, in 4 pages.
Urschel, J. D. et al., "The Effect of Mechanical Stress on Soft and Hard Tissue Repair; A Review", British Journal of Plastic Surgery, 1988, vol. 41, pp. 182-186, in 5 pages.
Vijanto, J. et al., "Local Hyperalimentation of Open Wounds", Br. J. Surg., 1976, vol. 63, pp. 427-430, in 4 pages.
Westaby, S. et al., "A Wound Irrigation Device", The Lancet, Sep. 2, 1978, pp. 503-504, in 2 pages.
Wooding-Scott, M. et al, "No Wound is Too Big for Resourceful Nurses," RN, Dec. 1988, pp. 22-25, USA, in 4 pages.
Zivadinovic, G. et al., "Vacuum Therapy in the Treatment of Peripheral Blood Vessels", Timocki Medicinski Glasnik (Conference Papers of the 5th Timok Medical Days, Majdanpek, 1986), Year XI, Zajecar, 1986, No. 3-4, with English translation, pp. 161-164, in 10 pages.

\* cited by examiner

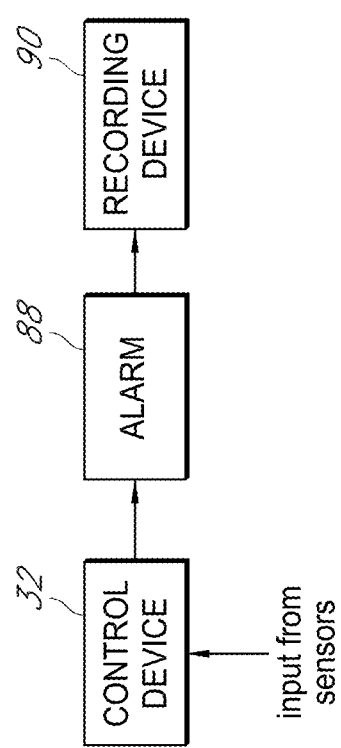

SUSTAINED VARIABLE NEGATIVE PRESSURE WOUND TREATMENT AND METHOD OF CONTROLLING SAME

CROSS-REFERENCE TO RELATED APPLICATIONS

This application is a continuation of U.S. patent application Ser. No. 14/945,935, filed on Nov. 19, 2015, which is a continuation of U.S. patent application Ser. No. 13/758,209, filed on Feb. 4, 2013, which is a continuation of U.S. patent application Ser. No. 12/812,232, filed on Jul. 8, 2010, which is a U.S. National Phase of PCT International Application No. PCT/US2009/030497, filed on Jan. 8, 2009, which claims the benefit of U.S. Provisional Patent Application No. 61/019,819, filed on Jan. 8, 2008. The disclosures of these prior applications are incorporated by reference in their entirety and should be considered a part of this specification.

BACKGROUND

Field of the Invention

Certain embodiments of the present application relate to treating a wound by applying reduced or negative pressure to the wound.

Description of the Related Art

The treatment of open or chronic wounds that are too large to spontaneously close or otherwise fail to heal has long been a troublesome area of the medical practice. Closure of an open wound requires inward migration of surrounding epithelial and subcutaneous tissue. Some wounds, however, are sufficiently large or infected that they are unable to heal spontaneously. In such instances, a zone of stasis in which localized edema restricts the flow of blood to the epithelial and subcutaneous tissue forms near the surface of the wound. Without sufficient blood flow, the wound is unable to successfully fight bacterial infection and is accordingly unable to close spontaneously.

An initial stage of wound healing is characterized by the formation of granulation tissue which is a matrix of collagen, fibronectin, and hyaluronic acid carrying macrophages, fibroblasts, and neovasculature that forms the basis for subsequent epithelialization of the wound. Infection and poor vascularization hinder the formation of granulation tissue within wounded tissue, thereby inhibiting wound healing. It therefore becomes desirable to provide a technique for increasing blood circulation within wounded tissue to promote spontaneous healing and to reduce infection.

Another problem encountered during the treatment of wounds is the selection of an appropriate technique for wound closure during the healing process. Sutures are often used to apply force to adjacent viable tissue in order to induce the edges of a wound to migrate together and heal. However, sutures apply a closure force to only a very small percentage of the area surrounding a wound. When there is scarring, edema, or insufficient tissue, the tension produced by the sutures can become great, causing excessive pressure to be exerted by the sutures upon the tissue adjacent to each suture. As a result, the adjacent tissue often becomes ischemic, thereby rendering suturing of large wounds counterproductive. If the quantity or size of the sutures is increased to reduce the tension required of any single suture, the quantity of foreign material within the wound is concomitantly increased and the wound is more apt to become infected. Additionally, the size or type of a particular wound may prevent the use of sutures to promote wound closure. It therefore becomes desirable to provide an apparatus and method for closing a large wound that distributes a closure force evenly about the periphery of the wound.

Wounds resulting from ischemia, or lack of blood flow, are also often difficult to heal since decreased blood flow to a wound may inhibit normal immune reaction to fight infection. Patients that are bedridden or otherwise non-ambulatory are susceptible to such ischemic wounds as decubitus ulcers or pressure sores. Decubitus ulcers form as a result of constant compression of the skin surface and underlying tissue thus restricting circulation. Since the patient is often unable to feel the wound or to move sufficiently to relieve the pressure, such wounds can become self-perpetuating. Although it is common to treat such wounds with flaps, the conditions that initially caused the wound may also work against successful flap attachment. Wheelchair-bound paraplegics, for example, must still remain seated after treatment of pelvic pressure sores. It therefore becomes desirable to provide a treatment procedure for ischemic wounds that can be conducted in situ upon an immobile or partially mobile patient.

Other types of wounds in which ischemia leads to progressive deterioration include partial thickness burns. A partial thickness burn is a burn in which the cell death due to thermal trauma does not extend below the deepest epidermal structures such as hair follicles, sweat glands, or sebaceous glands. The progression of partial thickness burns to deeper burns is a major problem in burn therapy. The ability to control or diminish the depth of burns greatly enhances the prognosis for burn patients and decreases morbidity resulting from burns. Partial thickness burns are formed of a zone of coagulation, which encompasses tissue killed by thermal injury, and a zone of stasis. The zone of stasis is a layer of tissue immediately beneath the zone of coagulation. Cells within the zone of stasis are viable, but the blood flow is static because of collapse of vascular structures due to localized edema. Unless blood flow is re-established within the zone of stasis soon after injury, the tissue within the zone of stasis also dies. The death of tissue within the zone of stasis is caused by lack of oxygen and nutrients, reperfusion injury (re-establishment of blood flow after prolonged ischemia), and decreased migration of white blood cells to the zone resulting in bacterial proliferation. Again, it becomes desirable to provide a technique for treating burn wounds by enhancing blood circulation to the wounded tissue to inhibit burn penetration. Negative pressure wound therapy has been around for many years and has been proven to assist with the healing of wounds.

SUMMARY

In some embodiments of the invention, reduced or negative pressure (e.g., below atmospheric pressure) can be used to assist with the healing of wounds, and can be used in three general modes. The first general mode is a continuous mode, wherein negative pressure is applied in a constant manner up to a predetermined pressure, where the negative pressure is held at this level. The second general mode may be characterized as being intermittent. In the intermittent mode, the negative pressure is preferably generally applied to the wound and then either released or disabled, allowing for a gentle or sudden release of the pressure back to atmospheric pressure. The third general mode, a variation of the intermittent mode, comprises application of the negative pressure to the wound at a first magnitude and then either releasing or disabling the pressure such that the negative pressure reaches a second magnitude. Application of intermittent pressure to the wound can assist patients with chronic, traumatic, and other type of wounds by healing such wounds in a rapid and efficient manner.

In some embodiments, such wounds are treated by using a negative pressure wound therapy apparatus preferably comprising a wound dressing, a fluid collection device, one or more conduits, filters, a suction source (e.g., a vacuum pump) configured to apply cyclical reduced pressure to the wound, and a control device configured to control the suction source. In some embodiments, cyclical reduced pressure may be applied to the wound between two or more magnitudes of pressure below atmospheric pressure and at one or more frequencies of cycling.

In some embodiments, the apparatus may comprise one or more sensors configured to monitor physiological conditions of a patient, such as temperature, pressure, blood flow, blood oxygen saturation, pulse, cardiac cycle, and the like. In some embodiments, the control device may receive the conditions monitored by the one or more sensor and control the suction source based on the monitored conditions.

In some embodiments, the apparatus may be configured to apply cyclical reduced pressure to the wound in synchrony with the monitored heart activity of the patient received from the one or more sensors. In some embodiments, the control device may control the suction source to apply a reduced pressure at a first amplitude during duration of systolic period, and to release the reduced pressure at the first amplitude to apply a reduced pressure at a second amplitude during duration of diastolic period. In some embodiments, the control device may control the suction source to apply a reduced pressure at a first amplitude during duration of diastolic period, and to release the reduced pressure at the first amplitude to apply a reduced pressure at a second amplitude during duration of systolic period. In some embodiments, the reduced pressure at the first amplitude may be applied during the entirety of systolic period and a part of diastolic period. In some embodiments, the reduced pressure at the first amplitude may be applied during the entirety of diastolic period and a part of systolic period. In some embodiments, cycling between the reduced pressure at the first amplitude and the reduced pressure at the second amplitude comprises varying reduced pressure according to a time-varying waveform such as a square, half-wave rectified trapezoid, and triangular waveforms and symmetric, half-wave rectified, asymmetric, and partially rectified asymmetric sinusoidal waveforms.

In some embodiments, the apparatus may be configured to apply cyclical reduced pressure to the wound in synchrony with the monitored blood flow through the wound received from the one or more sensors. In some embodiments, the apparatus may be configured to provide a baseline negative pressure of approximately 10-12 mmHg below atmospheric pressure, and to cycle the negative pressure by increasing the negative pressure applied to the wound by approximately 20-150 mmHg, at a frequency of approximately 20-60 cycles per minute. In some embodiments, to provide brief sustained levels of greater negative pressure, the apparatus may be configured for a baseline negative pressure of approximately 20 mmHg below atmospheric pressure, and for cycling the negative pressure by increasing it to approximately 200 mmHg below atmospheric pressure, at a frequency of approximately 120 cycles per minute.

In some embodiments, the apparatus may be configured to apply cyclical reduced pressure to the wound such that the reduced pressure at the second amplitude is between 5 and 85 mmHg above the reduced pressure at the first amplitude. In some embodiments, the apparatus may be configured to cycle the reduced pressure at the first and second amplitudes with a frequency of 200 to 400 cycles per minute.

In some embodiments, the apparatus can comprise an air reservoir and one or more valves and pressure sensors or gauges to allow for rapid cycling of the level of reduced pressure within the wound dressing between two or more reduced pressure values. The air reservoir, valves, and pressure sensors or gauges may be configured to supply positive pressure to the wound dressing from the air reservoir and reduced pressure to the wound dressing from the suction source. In some embodiments, the apparatus may be configured to comprise one or more conduits connecting the suction source and the air reservoir to the wound dressing. In some embodiments, the apparatus may comprise one or more safety valves.

In some embodiments, the air reservoir can be connected to the suction source and the wound dressing, and configured to supply positive pressure to the wound dressing. A control valve may be connected to the air reservoir and the wound dressing, the control valve may be configured to circulate air from the air reservoir into the wound dressing. In some embodiments, the apparatus can be configured to apply cyclical reduced pressure to the wound by closing the control valve during application of the reduced pressure at a first amplitude and opening the control valve during application of the reduced pressure at a second amplitude, such that opening the control valve circulates air from the air reservoir into the wound dressing.

Other embodiments of the invention are directed to methods for utilizing the apparatuses described above, and the subcomponents of the apparatuses described above. In one embodiment, a method for treating a wound of a patient is provided. A wound dressing is placed over and encloses the wound, the dressing adapted to maintain reduced pressure between the dressing and the wound. Reduced pressure is applied to the wound, wherein the applied reduced pressure is cycled between at least two different magnitudes of reduced pressure. In one embodiment, heart activity of the patient may be monitored, and the cycling is synchronized to the monitored heart activity. In another embodiment, positive pressure may be supplied to the wound dressing from an air reservoir. A control valve may be closed between the air reservoir and the wound dressing during application of reduced pressure at a first amplitude, and the control valve may be opened during application of reduced pressure at a second amplitude, wherein the opening of the control valve circulates air from the air reservoir into the wound dressing.

BRIEF DESCRIPTION OF THE DRAWINGS

These and other features, aspects and advantages will now be described in connection with certain embodiments, in reference to the accompanying drawings. The illustrated embodiments, however, are merely examples and are not intended to be limiting. The following are brief descriptions of the drawings.

FIG. 9 is a schematic representation of another embodiment of a sustained variable negative pressure wound treatment apparatus, illustrating control, recording, and alarm devices.

DETAILED DESCRIPTION OF THE PREFERRED EMBODIMENTS

Figure 1:
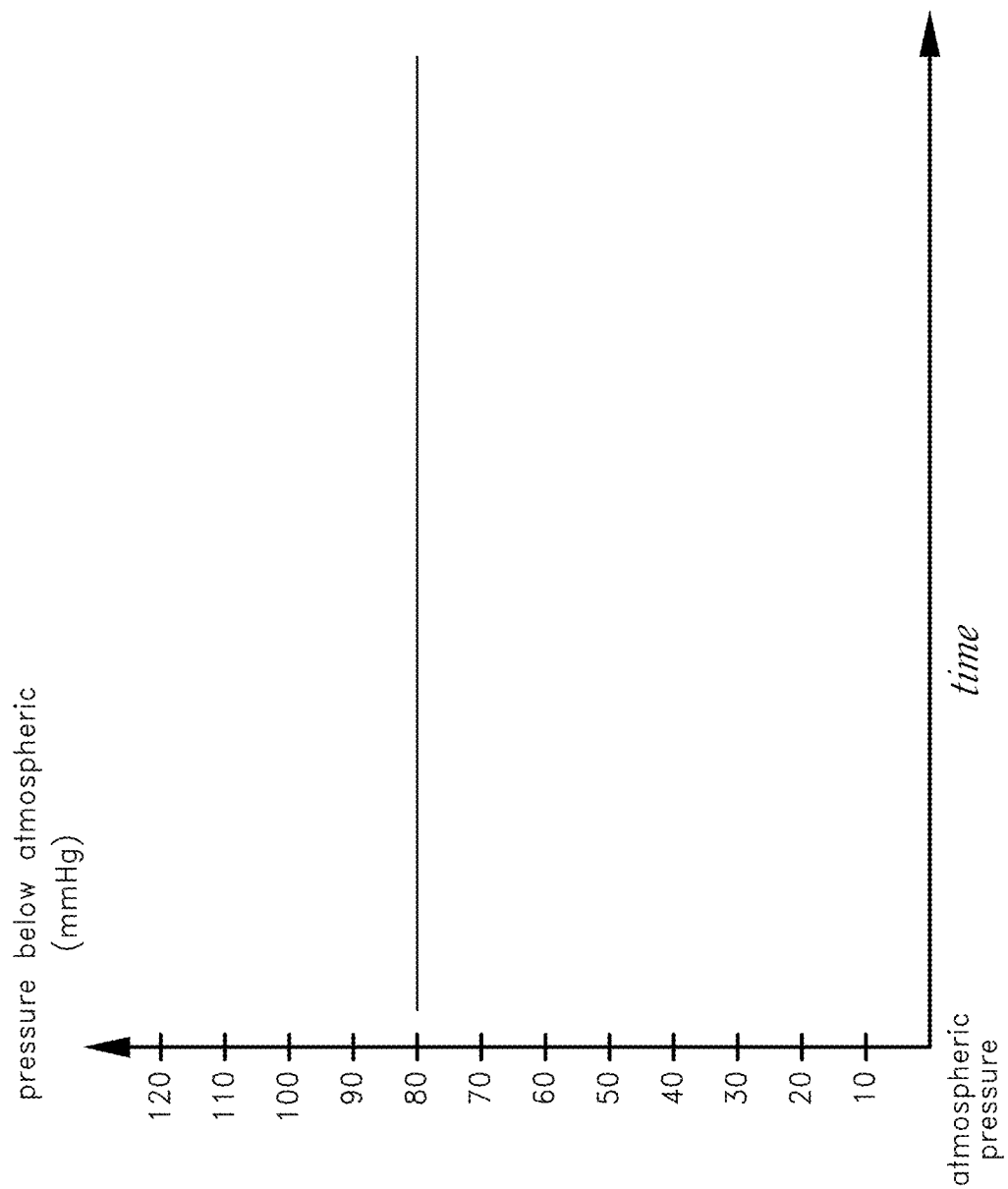
FIG. 1 is a schematic representation of a continuous reduced pressure program.

Negative pressure can be used to assist with the healing of wounds, and in certain embodiments of the invention, can be used in three general modes. The first general mode is a continuous mode, wherein negative pressure is applied in a constant manner up to a predetermined pressure, where the negative pressure is held at this level. For example, FIG. 1 illustrates continuous application to the wound site of negative pressure 80 mmHg below atmospheric pressure.

Figure 2:
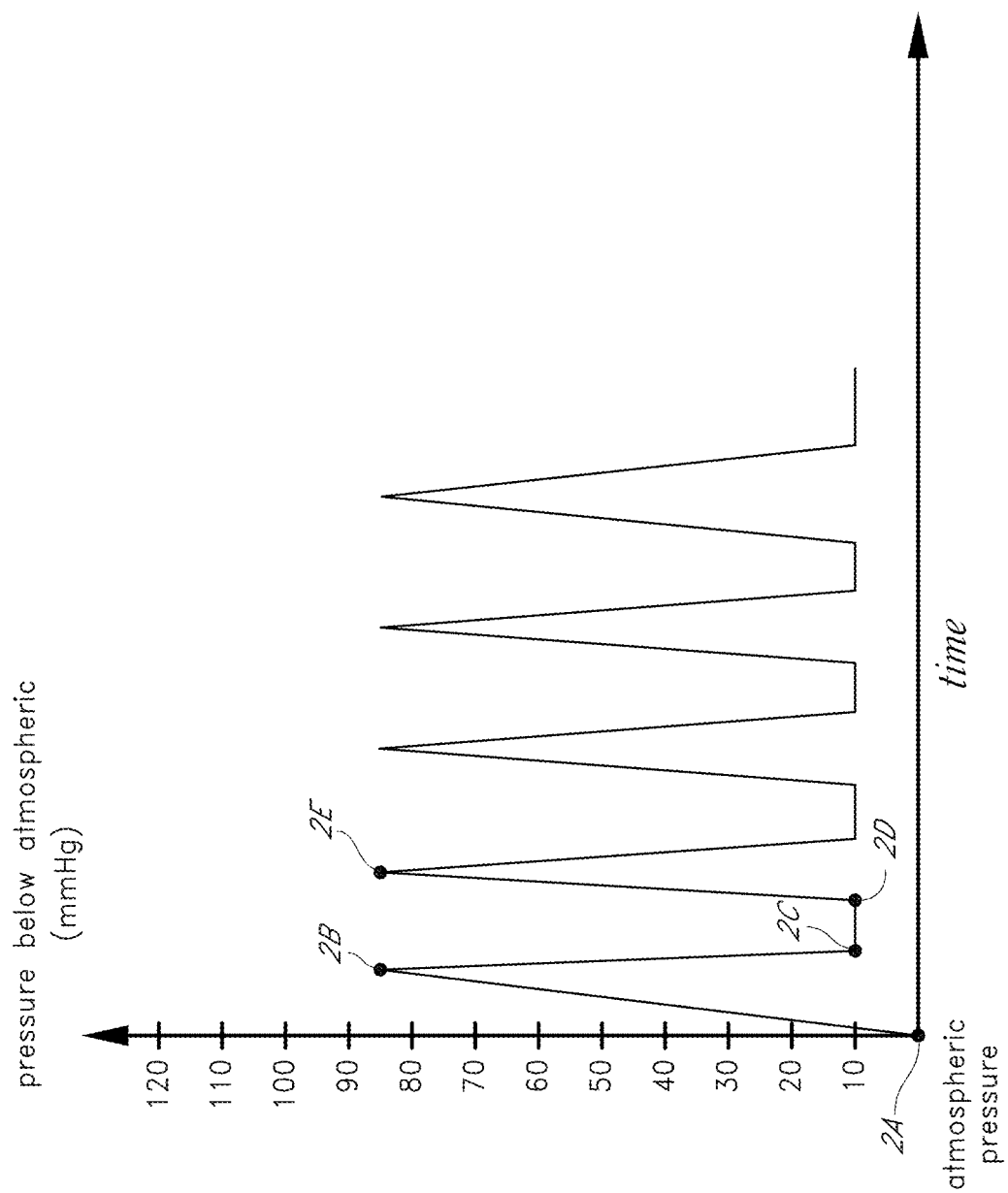
FIG. 2 is a schematic representation of a sustained variable reduced pressure program.

The second general mode may be characterized as being intermittent. In the intermittent mode, the negative pressure is preferably generally applied to the wound and then either released or disabled, allowing for a gentle release of the pressure back to atmospheric pressure. A variation of the intermittent mode, referred to herein as sustained variable negative or reduced pressure, comprises application of the negative pressure to the wound at a first magnitude and then either releasing or disabling the pressure such that the negative pressure reaches a second magnitude. For example, FIG. 2 illustrates application of sustained variable negative pressure to the wound by cycling between negative pressure amplitudes of approximately 85 mmHg and 10 mmHg below atmospheric pressure. As is illustrated in FIG. 2, negative pressure of about 10 mmHg below atmospheric pressure is first applied to the wound. Subsequently, the negative pressure is increased (e.g., spiked) to 85 mmHg below atmospheric pressure for a short duration, and then released back to about 10 mmHg below atmospheric pressure. Such treatment may be advantageous when a wound causes a lot of pain or when the healing has reached a plateau.

In some embodiments, the apparatus preferably provides sustained variable negative pressure, which may allow for greater versatility in the application of negative pressure wound treatment. At least some embodiments of the apparatus are preferably configured to allow a medical practitioner or patient to apply a negative pressure in any of the three general modes discussed above, or to switch from one mode to another during operation. In some embodiments, the cycle frequency and amplitude of sustained variable negative pressure that the apparatus can provide may be adjusted by a patient or a medical practitioner, or may be pre-programmed in the apparatus.

Sustained variable negative pressure wound treatment is a new and novel concept that can assist patients with chronic, traumatic, and other type of wounds by healing such wounds in a rapid and efficient manner. For example, delivery of sustained variable negative pressure can be synchronized to a patient's heartbeat to maintain better blood flow through the wound and to promote healing. As another example, delivery of sustained variable negative pressure can by decreasing the amplitude of pressure below capillary closing pressure, thus maintaining a higher level of blood flow through the wound.

Figure 3:
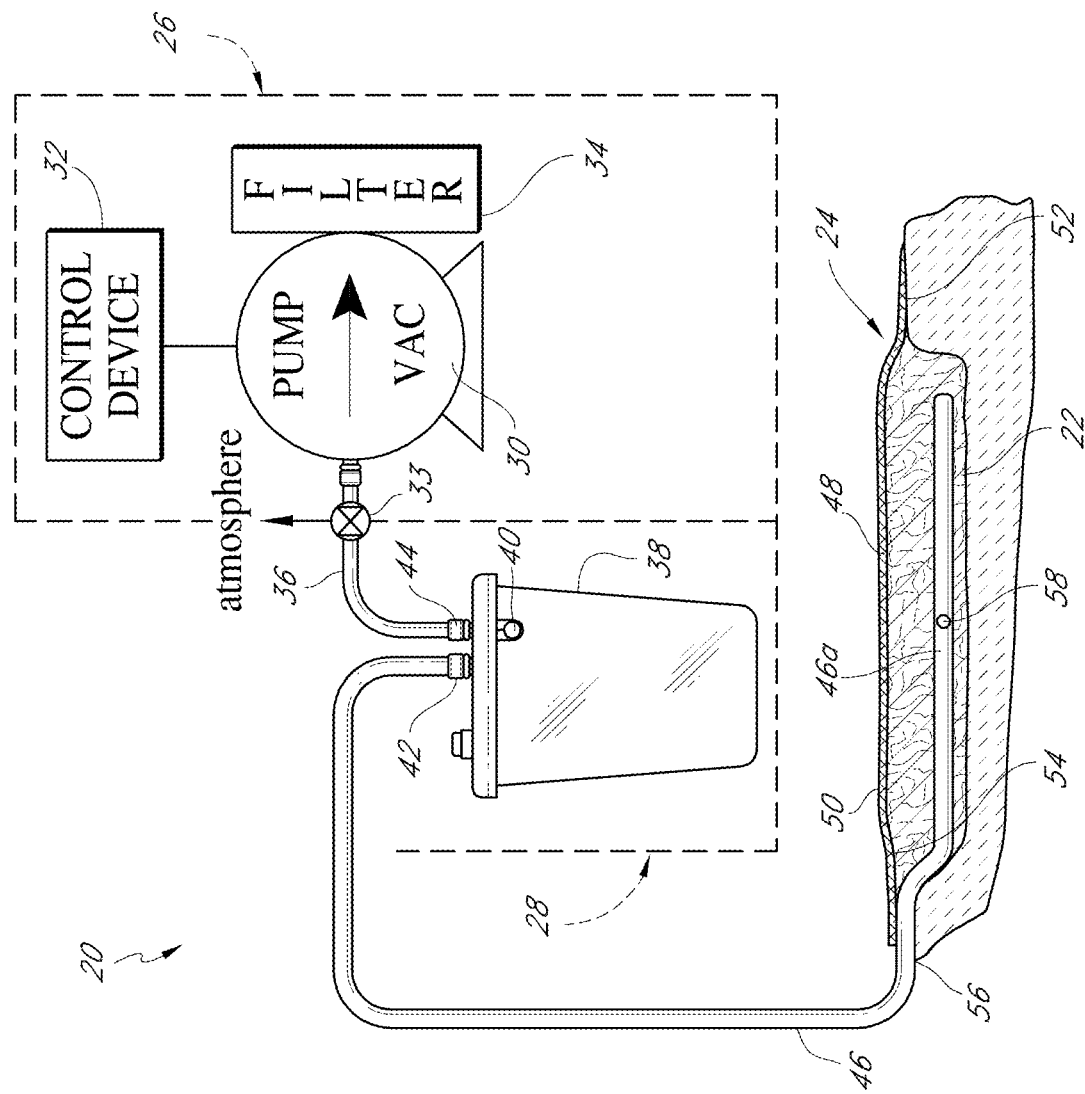
FIG. 3 is a schematic representation of an embodiment of a sustained variable negative pressure wound treatment apparatus.

FIG. 3 is a schematic view of an embodiment of a sustained variable negative pressure wound therapy apparatus 20. As described herein, a sustained variable negative pressure wound therapy apparatus may be configured to treat a wound by application of reduced pressure (e.g., below atmospheric pressure) to a wound site 22 at different amplitudes so as to provide sustained variable negative pressure to the wound site 22 in a controlled manner for a selected period of time.

As is illustrated in FIG. 3, the negative pressure wound therapy apparatus 20 comprises a wound cover or wound dressing 24 for enclosing a wound site 22 and providing a fluid-tight or gas-tight enclosure over the wound site 22 to effect treatment of a wound site 22 with sustained variable negative pressure. For the purpose of creating suction within the wound dressing 24, the wound dressing 24 is connected to a vacuum system 26 to provide a source of suction or reduced pressure for the sealed wound dressing 24 at the wound site 22. The suction source 26 may comprise a vacuum pump 30 that preferably cycles between at least two predetermined levels of negative pressure, the negative pressure being applied to a wound or wound dressing, wherein the predetermined levels of negative pressure are greater than zero such that a negative pressure is always applied to the wound or wound dressing. The suction source 26 may further comprise a control device 32, a filter 34, and tubing 36 that connects the vacuum pump 30 to a fluid collection system 28. Predetermined amounts of suction or reduced pressure are produced by the vacuum pump 30. The vacuum pump 30 is preferably controlled by a control device 32 that will be described in greater detail below. A filter 34, such as micropore filter, is attached to the exhaust of the vacuum pump 30 to prevent potentially pathogenic microbes or aerosols from the wound site 22 from being vented to the atmosphere by the vacuum pump 30. In some embodiments (not shown), the filter may preferably be positioned between the fluid collection system 28 and pump 30 along tubing 36 such that the pump may be protected from contaminated fluids. In some embodiments, the suction source 26 can comprise two or more vacuum pumps 30 (primary and secondary pumps) connected with tubing 36, preferably arranged in parallel. As described below, the additional pump may provide faster switching of reduced pressure cycles, increased suction, and a higher level of safety and product quality by providing pump redundancy to prevent a suction source failure in the event that a single pump fails. In some embodiments, the cycle frequency and amplitude of sustained variable negative pressure that the apparatus can provide can be adjusted by a patient or medical practitioner, or can be pre-programmed in the apparatus. For safety reasons, there may be limits as to how low or high the frequency and amplitude may be adjusted or pre-programmed.

Between the wound dressing 24 and the suction source 26 is a fluid collection system 28 for intercepting and retaining exudate that is aspirated from the wound site 22. The fluid collection system 28 is preferably interconnected between the suction vacuum pump 30 and wound dressing 24 to remove and collect any exudate which may be aspirated from the wound site 22 by the wound dressing 24. The wound dressing 24 preferably functions to actively draw fluid or exudate from the wound site 22. Collection of exudate in a fluid collection system 28 between the vacuum pump 30 and the wound dressing 24 is preferred to prevent clogging of the vacuum pump 30.

As illustrated in FIG. 3, the fluid collection system 28 may be comprised of a fluid-impermeable collection container 38 and a shutoff mechanism 40. The container 38 may be of any size and shape suitable for intercepting and retaining a predetermined amount of exudate. Many examples of such containers are available in the relevant art. The container 38 illustrated preferably has a first port 42 and a second port 44 positioned on the top of the container 38. The first port 42 preferably enables suction to be applied to the wound dressing 24 through the tubing 46 and also enables exudate from the wound site 22 covered by wound dressing 24 to be drained into the container 38. In some embodiments, the tubing 46 may comprise two or more tubes, with constant level of negative pressure and cycled negative pressure being applied through different tubes to a wound or wound dressing. In some embodiments, the tubing 36, 46 can be sized and configured to conduct enough air to permit the apparatus to rapidly cycle the level of reduced pressure within the dressing 124 between two or more reduced pressure values. The container 38 provides a means for containing and temporarily storing the collected exudate. A second port 44 is also provided on the top of the container 38 to enable the application of suction from the vacuum pump 30 to the container 38. As mentioned above, the second port 44 of the collection system 28 is connected to the vacuum pump 30 by a vacuum line 36. The collection system 28 is preferably sealed approximately gas-tight so that as to enable the suction vacuum pump 30 to supply suction to the wound dressing 24 through the collection system 28.

The fluid-impermeable wound cover 50 in the embodiment of the wound dressing 24 illustrated in FIG. 3 may be substantially rigid (to better support application of cyclical negative pressure) or flexible sheet. The sheet may also include an adhesive, and may be a fluid impermeable polymer sheet for covering and enclosing the wound site 22, including an optional absorbable matrix 48 within it, and the surrounding normal skin 52 around the wound site 22. In some embodiments, the wound cover 50 may be of biologically created material, such as artificially grown skin. In further embodiments the matrix 48 may be non-bioabsorbable, as is known in the art. The wound cover 50 preferably includes an adhesive backing 54 which functions to seal the wound cover 50 to the normal skin 52 around the periphery of the wound site 22 so as to provide a generally gas-tight or fluid-tight enclosure over the wound site 22. The adhesive cover 50 preferably has sufficient adhesion to form a fluid-tight or gas-tight seal around the periphery of the wound site 22 and to hold the cover 50 in sealed contact with the skin 52 during the application of suction, reduced or negative pressure, or cycled negative pressure. The wound cover 50 also preferably provides a gas-tight seal around the tubing 46 at the feedthrough location 56 where the tubing 46 emerges from beneath the wound cover 50. The tube segment 46a embedded within the absorbable matrix 48 preferably has at least one side port 58 positioned within the interior of the absorbable matrix 48 to enable a substantially uniform application of reduced pressure throughout the enclosure. In some embodiments (not shown), the tubing 46 may be connected to the wound dressing 24 through a port positioned on the top of the dressing.

In some embodiments, the wound dressing 24 may also comprise an intermittent layer (not shown) configured to evenly distribute the suction over the wound. The intermittent layer may contain a variety of materials that partially collapse under application of negative pressure, such as gauze and gauze type materials, open cell foams, sponges, matrix type materials, and the like.

The absorbable matrix 48 can be placed over substantially the expanse of the wound site 22 to encourage growth of tissue in the area of the wound site 22 into the matrix 48 as the wound heals. The size and configuration of the absorbable matrix 48 can be adjusted to fit the individual wound site 22. It can be formed from a variety of absorbable materials, preferably a material that is also porous. The matrix 48 should be constructed in a manner so that it is sufficiently porous to allow oxygen to reach the wound site 22. The absorbable matrix 48 is preferably constructed of a non-toxic material that is absorbable by the epithelial and subcutaneous tissue within the area of the wound site 22, such as collagens derived from healthy mammals, absorbable synthetic polymers, or other materials similar to those used for absorbable dressings. However, other materials for and configurations of the absorbable matrix 48 can be used with the negative pressure wound therapy apparatus 20 disclosed herein, such as is described in U.S. Patent Application Publication No. US 2004/0073151 A1, which is incorporated by reference herein in its entirety.

In some embodiments, the apparatus may comprise a dressing 24 that is configured to distribute the negative pressure approximately evenly to all portions of the wound. Alternatively, in some embodiments the apparatus may comprise a dressing that is configured to distribute the negative pressure at different levels to different portions of the wound. For example, in some embodiments, if a sensor (as described below) determines that the blood oxygen level flowing into a portion of the wound is lower than optimal value, the dressing would preferably be configured to provide an increased level of negative pressure to that particular portion of the wound. Further as mentioned above, the dressing may have a stronger seal or sealing aspect so as to minimize the incidence of any leaks in the dressing during the cyclic loading of negative pressure.

The suction source 26 can be provided by any suitable device such as, but not limited to, a portable suction pump apparatus, a piston type device, several pistons in combination, a diaphragm type pump, a rotary vane pump, or the like. The suction source can also originate from wall suction (as is provided in hospitals), and a regulator could be attached to the wall suction source. As described above, the suction source can be provided by a vacuum pump. A second pump may be used to provide faster switching of reduced pressure cycles, increased suction, and a higher level of safety and product quality by providing pump redundancy to prevent a suction source failure in the event that a single pump fails. Alternatively, a single large volume vacuum pump may be used to provide switching of reduced pressure cycles and increased suction. Alternatively, the vacuum pump may have a secondary piston or diaphragm that provides for faster switching of reduced pressure cycles, increased suction, and a higher level of safety and product quality.

The vacuum pump may decrease or release the negative pressure applied during cycling of negative pressure by releasing the pressure through a port or valve in the pump or in the dressing, or by turning off the pump source and allowing inherent leaks in the dressing drop the pressure down. As shown in FIG. 3, a valve 33 may be placed along tubing 36 to release the negative pressure applied during cycling. A filter (not shown), such as micropore filter, may be attached to the port or valve to prevent potentially pathogenic microbes or aerosols from the wound site 22 from being vented to the atmosphere.

A control device 32 can control the vacuum pump so as to control the amount of suction that is provided to the dressing 24 and wound site. The control device 32 preferably receives signals from the sensors and converts the signals to an electronic or other suitable form that can be recognized by the vacuum pump. In some embodiments, the control device 32 can be configured to operate without a processor. For example, the control circuit and other aspects of the apparatus disclosed in International Patent Application Publication No. WO 2008/048481, can be used to control the pump motor or pump described herein. Additionally, any of the configurations described in the above-mentioned WO 2008/048481 application publication regarding pressure sensors, the control of such pressure sensors, and/or other aspects of the apparatus disclosed therein can be used with the apparatus described in the present application, and International Patent Application Publication No. WO 2008/048481 is hereby incorporated by reference as if fully set forth herein.

In some embodiments, the control device 32 can comprise a processor that preferably enables the control device to control the vacuum pump 30 or, as described below, the wound dressing, valves, pressure sensors, or other components comprising the apparatus. Furthermore, the control device 32 can be a computer, data processor, or other controller having any suitable device such as, but not limited to, a processor, for controlling the pump motors and/or other components that are described herein, or for receiving or changing data, or for any other function suitable for the apparatus. In some embodiments, a control device comprising digital componentry, i.e., comprising digital electronics and microprocessors, may improve the robustness of the pump in the sustained variable pressure mode.

Figure 4A:
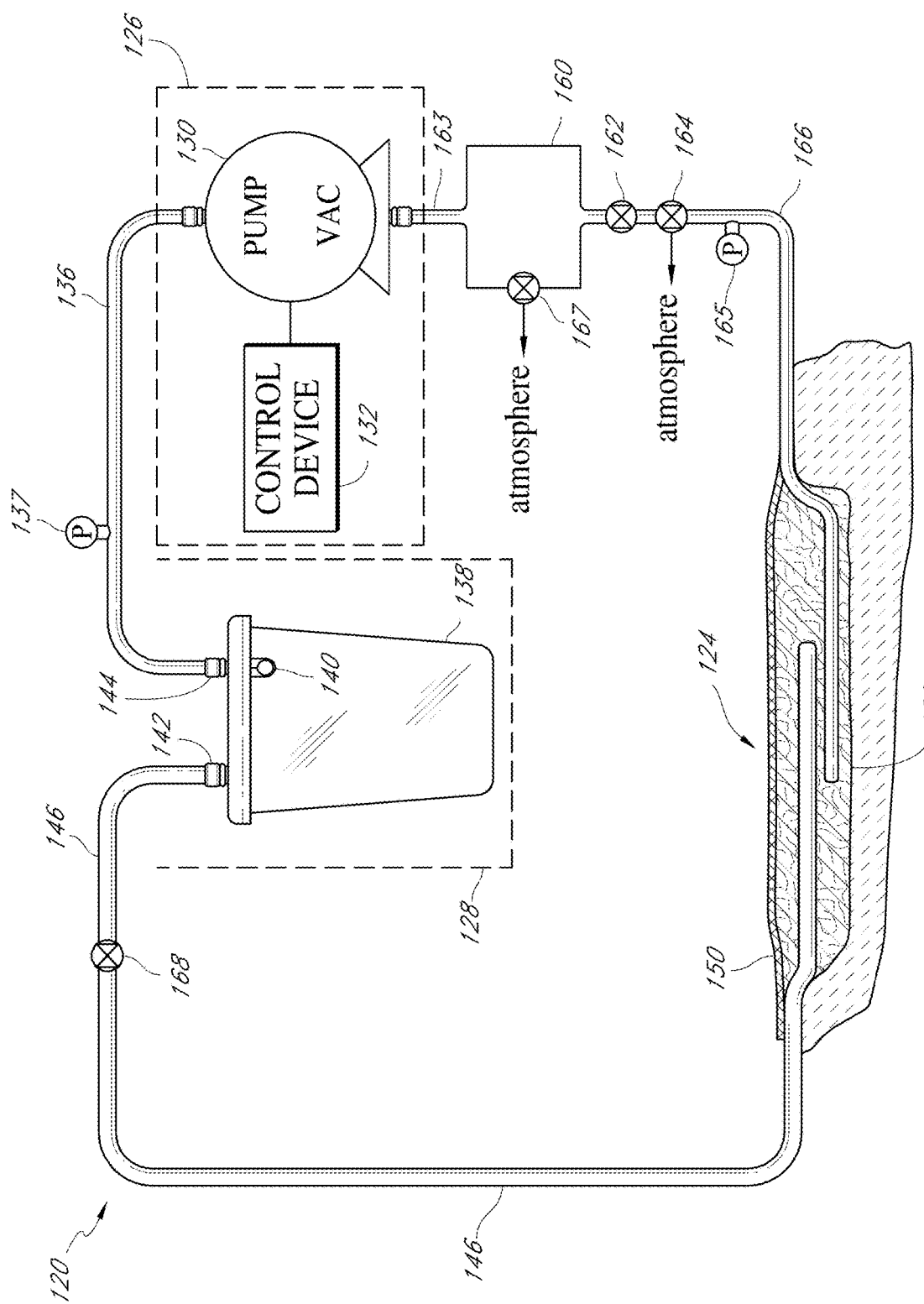
FIG. 4A is a schematic representation of another embodiment of a sustained variable negative pressure wound treatment apparatus.

FIG. 4A is a schematic view of another embodiment of a sustained variable negative pressure wound therapy apparatus 120. As illustrated in FIG. 4A, some embodiments of the sustained variable negative pressure wound therapy apparatus 120 can have any of the same components, features, materials, or other details, including but not limited to the fluid collection system, wound cover, wound filler, valves, and/or pressure sensors, as in any other negative pressure wound therapy apparatuses disclosed herein or otherwise known or later developed in the field.

As will be described in greater detail below, the negative pressure wound therapy apparatus 120 can comprise a wound dressing 124 configured to cover the wound site 122, a suction source 126, a fluid collection system 128 that can have a collection container 138, a shutoff mechanism 140, a first port 142, and a second port 144 positioned on the top of the container 138, and an air reservoir 160. As will be described in greater detail below, the air reservoir 160 can enable the negative pressure wound therapy apparatus 120 to quickly change the level of reduced pressure within the wound dressing 124 to allow for rapid cycling of the level of reduced pressure within the wound dressing 124. Conduit or tubing 136 can be used to communicate or supply reduced pressure from the vacuum pump 130 to the collection container 138, and conduit or tubing 146 can be used to communicate or supply reduced pressure from the collection container 138 to the wound site 122, by being routed under the wound dressing 124. Additionally, conduit or tubing 163 can be used to communicate or supply increased pressure from the vacuum pump 130 to the air reservoir 160 and conduit or tubing 166 can be used to communicate or supply increased pressure from the air reservoir 160 to the wound site 122, by being routed under the wound cover 124.

As used herein, the term increased pressure is used to describe the air that is exhausted by the vacuum pump 130 as the vacuum pump 130 reduces the air pressure within the conduit 136. In some conventional systems or apparatuses, the increased pressure or exhaust air from a vacuum pump is typically exhausted to the atmosphere. In the apparatus 120, however, the increased pressure or exhaust air from the vacuum pump 130 can be directed into the air reservoir 160 to be used to quickly increase the air pressure within the wound dressing 124 so that the level of reduced pressure within the wound dressing 124 can be cycled between two or more reduced pressure values, as is described herein.

In some embodiments, the suction source 126 can comprise a vacuum pump 130 and control device 132. A filter, such as micropore or other suitable filter (not shown), can be positioned between the vacuum pump 130 and the air reservoir 160. The filter can cleanse the exhaust air flowing out of the vacuum pump 130 to prevent or reduce the amount of bacteria, potentially pathogenic microbes or aerosols, or other contamination from the vacuum pump 130 exhaust air before the air is channeled into the air reservoir 160. Additionally, the vacuum pump 130 can be configured to vent a portion of the air removed from the conduit 136 to the atmosphere. In this configuration, a filter (not shown), such as a micropore or other suitable filter, can be positioned between the vacuum pump 130 and the atmosphere. The filter can cleanse the exhaust air flowing out of the vacuum pump 130 to prevent or reduce the amount of potentially harmful bacteria or microbes from entering the atmosphere.

Each of the components comprising the suction source 126 can be the same as or similar to any of the components comprising the suction source of any other apparatuses described herein or otherwise known or later developed in the field. In some embodiments, as will be described in greater detail below, the control device 132 can be configured to control the vacuum pump 130 and any of the valves used in the apparatus 120. Additionally, the control device 132 can be configured to receive and process signal inputs from each of the pressure sensors positioned within the apparatus 120, and to control each of the valves and vacuum pump based on, without limitation, the pressure sensor readings and predetermined reduced pressure loading programs.

A pressure sensor or gauge 137 can be positioned along tubing 136 that connects the suction source 126 to the collection container 138. The pressure sensor 137 can be used to monitor the pressure within the conduit 136. In this configuration, the pressure sensor 137 can be used to determine the approximate air pressure within the wound dressing 124. Additional valves and pressure sensors can be positioned at any desired location within the apparatus 120 to further monitor and control the pressure within any desired location of the apparatus 120. For example, if desired, additional pressure sensors can be positioned at various locations within the apparatus 120 such as, but not limited to, in the tubing 146 connecting the fluid collection system 128 to the wound dressing 124.

A valve 168 can be positioned along tubing 146 as shown. Any of the valves described herein can be actuated by the control device 132 and can be used to control the amount of air flow through the conduit in which the valve is positioned. As such, the valve 168 can be controlled by the control device 132 to substantially prevent, allow, or otherwise control the level of air flow through the conduit 146. In this configuration, the valve 168 can be used to provide an approximate seal between the fluid collection system 128 and the wound dressing 124.

As mentioned, an air reservoir 160 can be connected to the suction source 126 with tubing 163. The reservoir 160 can be configured to have any suitable size, volume, or shape desired. In some embodiments, the air reservoir 160 can be sized and configured to hold enough air to permit the apparatus 120 to rapidly cycle the level of reduced pressure within the dressing 124 between two or more reduced pressure values. The reservoir 160 can have a valve 167, which can vent air from the air reservoir 160 to the atmosphere. The valve 167 can be a safety release valve configured to prevent the air reservoir 160 or any other components within the apparatus 120 from rupturing from excessive air pressure. In some embodiments, a filter (not shown), such as micropore filter, may be attached to the valve 167 to prevent potentially pathogenic microbes or aerosols from the wound site 122 from being vented to the atmosphere.

A valve 162 can be positioned along the tubing 166 as shown. As described above, the valve 162 can be configured to control the amount of air flowing through the conduit 166. As such, the valve 162 can be closed by the control device 132 to provide an approximate seal between the air reservoir 160 and the wound dressing 124. Additionally, a valve 164 can be positioned along the tubing 166 as shown in FIG. 4A and can be used to release the pressure from the wound dressing 124 and the tubing 166. A pressure sensor or gauge 165 can be positioned along the tubing 166 to monitor the pressure in the tubing 166 and, hence, in the wound dressing 124.

An additional pressure sensor (not shown) can be positioned in the conduit 163 or in the air reservoir 160 to monitor the level air pressure between the vacuum pump 130 and the valve 162. This additional pressure sensor (not shown), can be useful to monitor the level of pressure within the air reservoir 160 when the valve 162 is closed. Similarly, an additional pressure sensor (not shown) can be positioned within the tubing 146 between the wound dressing 124 and the valve 168 to monitor the level of pressure within the tubing 146 and, hence, the wound dressing 124, when the valve 168 is closed.

The fluid-impermeable wound cover 150 in the embodiment of the wound dressing 124 illustrated in FIG. 4A preferably provides an approximately gas-tight seal around the tubing 146 and 166 where the tubing 146 and 166 emerges from beneath the wound cover 150. In some embodiments (not shown), one or more of the tubing 146 and 166 may be connected to the wound dressing 124 through a port or ports integrally formed or otherwise attached to the wound cover 150.

In some embodiments, a valve that can be configured to selectively permit air to enter the conduit 146 from the atmosphere can be positioned along the tubing 146 between the valve 168 and the collection container 138. This valve may be used to quickly provide air to the conduit 146 and, hence, the wound dressing 124 during operation of the apparatus 120 to rapidly decrease the level of reduced pressure within the conduit 146 and the wound dressing 124. A filter, such as micropore filter, may be attached to the valve to prevent bacteria, germs, microbes, or other contaminants from the outside air from entering into the tubing 146 and wound dressing 124.

In some embodiments, a filter, such as micropore or other suitable filter, can be positioned between the vacuum pump 130 and the collection container 138 (for example, without limitation, at port 144 or otherwise supported by the collection container 138) to prevent or reduce the amount of exudate, bacteria, potentially pathogenic microbes or aerosols, or other contamination from the wound site 122 from entering the vacuum pump 130. Another filter, such as micropore or other suitable filter, can be positioned in the tubing 166 to prevent or reduce the amount of exudate, bacteria, potentially pathogenic microbes or aerosols, or other contamination from the wound site 122 from entering the vacuum pump 130, and to prevent or reduce the amount of bacteria, potentially pathogenic microbes or aerosols, or other contamination from entering the wound site 122. The filters described herein may additionally be disposable and intended for single patient use.

In some embodiments, the apparatus 120 may be used to provide sustained variable negative pressure as follows. With reference to FIG. 2, point 2A represents the level of reduced pressure with wound dressing before the suction system 126 has been actuated and, hence, before the pressure within the dressing 124 has been reduced. In other words, point 2A represents atmospheric pressure. In order to increase the level of reduced or negative pressure within the wound dressing 124, the valve 168 can be opened and valve 162 can be closed when the pump 130 is actuated. Additionally, the valves 164 and 167 can be closed at this point to prevent increased pressure from venting to the atmosphere. Thus, in this configuration, when the vacuum pump 130 is actuated, the reduced or negative pressure within the dressing 124 can be increased from point 2A to point 2B (as can be monitored by the pressure sensor 137), which is approximately 85 mmHg. Again, the values described herein and are meant to be approximate and merely exemplifying. As such, the values set forth herein are non-limiting. The apparatus 120 or any other apparatus described herein can be configured to provide any suitable or desired level of negative or reduced pressure at any suitable or desired frequency.

As the pump 130 draws air out of the conduits 136, 146 and, hence, increases the level of reduced pressure within the wound dressing 124 from point 2A to point 2B, the air that is drawn out of conduits 136, 146 can be channeled into the air reservoir 160. In other words, the level of positive pressure within the reservoir 160 can be increased with the air that is drawn out of the wound dressing 124, while the level of negative pressure in the wound dressing 124 is being increased. Once the level of reduced pressure within the wound dressing 124 has reached point 2B, the vacuum pump 130 can be stopped and the valve 168 can be closed.

In some embodiments, the vacuum pump 130 can be configured such that air can only flow through the vacuum pump 130 in one direction, to substantially prevent air from flowing from the air reservoir 160 through the vacuum pump 130 into the conduit 136. Additionally, the vacuum pump 130 can be sized and configured to provide as rapid an increase in the reduced pressure as is desired. In some embodiments of the apparatus 120, multiple vacuum pumps or multi-piston pumps 130 can be used to increase the rate of air flow through the apparatus 120, so that the level of reduced pressure within the wound dressing 124 can be cycled at any desired amplitude or frequency.

After the level of reduced pressure within the dressing 124 has reached point 2B, the valve 162 can be opened by the control device 132 and the valve 168 can be closed by the control device 132 or remain closed. In some embodiments, the valves 162, 168 can be simultaneously opened and closed, respectively, or the valves 162, 168 can be sequentially opened and closed, respectively. With valve 162 open and a valve 168 closed, positive pressure or air within the air reservoir 160 can be transferred from the air reservoir 160 to the volume beneath the wound dressing 124, so as to decrease the level of reduced pressure within the dressing from point 2B to point 2C. Consequently, air will be caused to fill the conduit 146 up to the valve 168, causing the level of reduced pressure within that portion of the conduit 146 to be decreased to point 2C. Once the level of reduced pressure within the volume beneath the wound dressing 124 has reached point 2C, as can be monitored by the pressure sensor 165, the valve 162 can be closed by the control device 132 so that the level of pressure within the wound dressing 124 is maintained at approximately point 2C.

Thereafter, the level of reduced pressure within the dressing 124 can be maintained at a constant level for a period of time (i.e., from point 2C to point 2D), or it can be approximately immediately increased, such as to the level represented by point 2E. To increase the level of reduced pressure from point 2C or point 2D to point 2E, with the valve 162 closed, the vacuum pump 130 can again be actuated and the valve 168 can be opened, causing the vacuum pump to again draw air from the conduits 136, 146 and the volume beneath the wound dressing 124 until the level of pressure within the wound dressing reaches a desired level, such as the level represented by point 2E. When this period elapses, the cycle can repeat as described above. Thus, in this configuration, by circulating the air through the apparatus 120 as described above, the level of reduced pressure within the volume beneath the wound dressing 124 can be rapidly cycled.

Additionally, by positioning the valve 168 as close as it is feasible to the wound dressing 124 and by reducing the volume within each of the conduits, the volume of the negative pressure airspace that is required to be increased and decreased can be reduced, thus permitting the apparatus 120 to accommodate higher frequencies of sustained variable pressure. In some embodiments where cycling of negative pressure comprises small variations in the magnitude of negative pressure (e.g. 10 mmHg), the air reservoir 160 may not be needed. In such cases, valve 164 may be closed or valve 167 may be opened to not involve the reservoir 160 in the cycling. In some embodiments, the vacuum pump 130 may be configured to be reversible, such that the level of reduced pressure within the wound dressing 124 can be increased and decreased just by the operation of the vacuum pump 130.

Figure 4B:
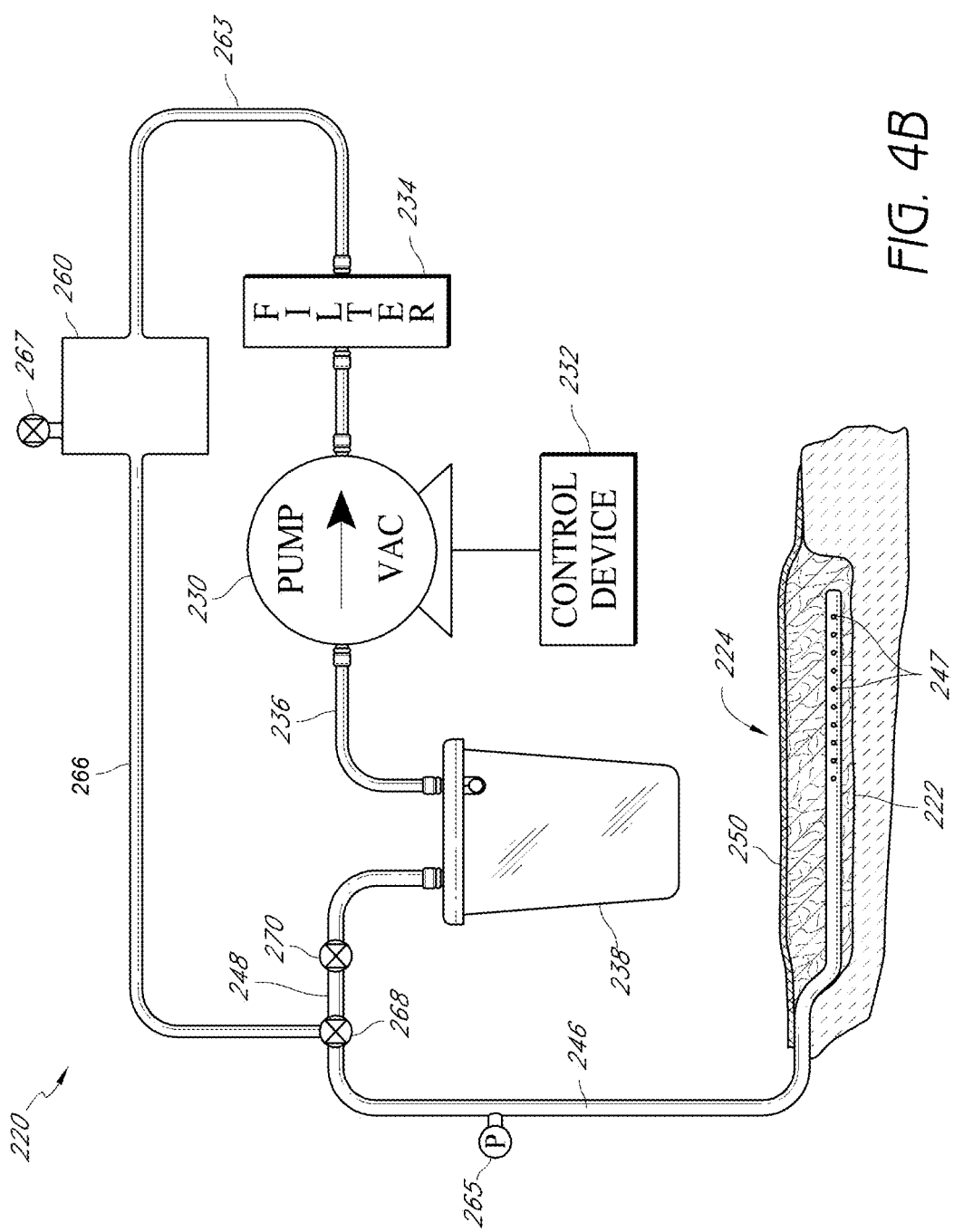
FIG. 4B is a schematic representation of another embodiment of a sustained variable negative pressure wound treatment apparatus.

FIG. 4B is a schematic view of another embodiment of a sustained variable negative pressure wound therapy apparatus 220. As illustrated in FIG. 4B, some embodiments of the sustained variable negative pressure wound therapy apparatus 220 can have any of the same components, features, materials, or other details, including but not limited to the fluid collection system, wound cover, wound filler, valves, and/or pressure sensors, as in any other negative pressure wound therapy apparatuses disclosed herein or otherwise known or later developed in the field.

As will be described in greater detail below, the negative pressure wound therapy apparatus 220 can comprise a wound dressing 224 configured to cover the wound site 222, a vacuum pump 230, a control device 232, a fluid collection system 238, and an air reservoir 260. Similar to the air reservoir 160 described above, the air reservoir 260 can enable the negative pressure wound therapy apparatus 220 to quickly change the level of reduced pressure within the wound dressing 224 to allow for rapid cycling of the level of reduced pressure within the wound dressing 224. Conduit or tubing 236 can be used to communicate or supply reduced pressure from the vacuum pump 230 to the fluid collection system 238, and conduit or tubing 246 can be used to communicate or supply reduced pressure from the fluid collection system 238 to the wound site 222, by being routed under the wound dressing 224. In some embodiments, the conduit 246 can have openings 247 in the end portion of the conduit 246 to distribute the pressure within the conduit 246. Additionally, conduit or tubing 263 can be used to communicate or supply increased pressure from the vacuum pump 230 to the air reservoir 260 and conduit or tubing 266 can be used to communicate or supply increased pressure from the air reservoir 260 to the wound site 222, by being routed under the wound dressing 224. As illustrated in FIG. 4B, the conduit 266 can be joined with conduit 248 by using a valve 268 positioned at the juncture of conduit 248 and 266.

The valve 268 can be controlled by the control device 232 and can be used to permit the conduit 246 to communicate either with conduit 248 or conduit 266, independently. In other words, when the valve 268 is in a first position, the conduit 246 will be permitted to communicate with the conduit 248 but not with conduit 266. In this first position, air and/or fluid will be permitted to flow from conduit 246 to conduit 248, but air and/or fluid will not be permitted to flow from conduit 246 or conduit 248 to conduit 266. When the valve 268 is in a second position, the conduit 246 will be permitted to communicate with the conduit 266 but not with conduit 248. In this second position, air and/or fluid will be permitted to flow from conduit 266 to conduit 246, but air and/or fluid will not be permitted to flow from conduit 266 to conduit 246 or 248. A valve 270 can be positioned within the conduit 248 to permit or prevent air and/or fluid from flowing through conduit 248. However, valve 270 is not required for the operation of the apparatus 220.

As mentioned above, in the apparatus 220, the increased pressure or exhaust air from the vacuum pump 230 can be directed to the air reservoir 260 to be used to quickly increase the air pressure within the wound dressing 224 so that the level of reduced pressure within the wound dressing 224 can be rapidly cycled between two or more reduced pressure values, as is described herein.

In some embodiments, a filter 234, which can be a micropore or other suitable filter, can be positioned between the vacuum pump 230 and the air reservoir 260. The filter can cleanse the exhaust air flowing out of the vacuum pump 230 to prevent or reduce the amount of bacteria, potentially pathogenic microbes or aerosols, or other contamination from the vacuum pump 230 exhaust air before the air is channeled into the air reservoir 260. In some embodiments, a filter (such as, without limitation, filter 234), which can be a micropore or other suitable filter, can be positioned in the conduit 236 to prevent or reduce the amount of exudate, bacteria, potentially pathogenic microbes or aerosols, or other contamination from the wound site 222 from entering the vacuum pump 230. In some embodiments, a micropore or other suitable filter (such as, without limitation, filter 234), can be positioned in the outlet port of the collection system 238 or otherwise be supported by the collection system 238. Additionally, in some embodiments, a micropore or other suitable filter can be positioned between the valve 268 and the reservoir 260 to prevent contamination from being circulated to the wound site 222 and/or from entering the vacuum pump 230.

Additionally, the vacuum pump 230 can be configured to vent a portion of the air removed from the conduit 236 to the atmosphere. In this configuration, a filter, such as a micropore or other suitable filter, can be positioned between the vacuum pump 230 and the atmosphere. The filter can cleanse the exhaust air flowing out of the vacuum pump 230 to prevent or reduce the amount of potentially harmful bacteria or microbes from entering the atmosphere.

In some embodiments, as will be described in greater detail below, the control device 232 can be configured to control the vacuum pump 230 and any of the valves used in the apparatus 220. Additionally, the control device 232 can be configured to receive and process signal inputs from each of the pressure sensors positioned within the apparatus 220, and to control each of the valves and vacuum pump based on, without limitation, the pressure sensor readings and predetermined reduced pressure loading programs.

A pressure sensor or gauge 265 can be positioned so as to be in communication with tubing 246 that communicates or supplies reduced pressure to the wound site 222. The pressure sensor 265 can be used to monitor the pressure within the conduit 246 and, hence, the pressure within the volume beneath the wound dressing 224. Additional valves and pressure sensors can be positioned at any desired location within the apparatus 220 to further monitor and control the pressure within any desired location of the apparatus 220. For example, if desired, additional pressure sensors can be positioned at various locations within the apparatus 220 such as, but not limited to, in the tubing 266 connecting the air reservoir 260 to the valve 268.

As mentioned, an air reservoir 260 can be connected to the vacuum pump 230 with tubing 263. The reservoir 260 can be configured to have any suitable size, volume, or shape desired. In some embodiments, the air reservoir 260 can be sized and configured to hold enough air to permit the apparatus 220 to rapidly cycle the level of reduced pressure within the wound dressing 224 between two or more reduced pressure values. The reservoir 260 can have a valve 267, which can vent air from the air reservoir 260 to the atmosphere. The valve 267 can be a safety release valve configured to prevent the air reservoir 260 or any other components within the apparatus 220 from rupturing from excessive air pressure. In some embodiments, a filter (not shown), such as micropore filter, may be attached to the valve 267 to prevent potentially pathogenic microbes or aerosols from the wound site 222 from being vented to the atmosphere.

The fluid-impermeable wound cover 250 in the embodiment of the wound dressing 224 illustrated in FIG. 4B preferably provides an approximately gas-tight seal around the tubing 246 where the tubing 246 emerges from beneath the wound cover 250. In some embodiments (not shown), the conduit 246 may be connected to the wound dressing 224 through a port integrally formed or otherwise attached to the wound cover 250.

In some embodiments, a valve that can be configured to selectively permit air to enter the conduit 246 from the atmosphere can be positioned along the tubing 246 between the valve 268 and the wound dressing 224. This valve may be used to quickly provide air to the conduit 246 and, hence, the wound dressing 224 during operation of the apparatus 220 to rapidly decrease the level of reduced pressure within the conduit 246 and the wound dressing 224. A filter, such as micropore filter, may be attached to the valve to prevent bacteria, germs, microbes, or other contaminants from the outside air from entering into the tubing 246 and wound dressing 224.

In some embodiments, the apparatus 220 may be used to provide sustained variable negative pressure as follows. With reference to FIG. 2, in order to increase the level of reduced or negative pressure within the wound dressing 224, the valve 268 can be positioned (by the control device 232) in the first position so that air can flow from conduit 246 into the conduit 248, but not into the conduit 266, when the pump 230 is actuated. Additionally, the valve 270 can be opened to permit air and/or fluid to flow through conduit 248 and into the collection container 238, and the valve 267 can be closed to prevent increased pressure from venting to the atmosphere. Thus, in this configuration, when the vacuum pump 230 is actuated, the reduced or negative pressure within the dressing 224 can be increased from point 2A to point 2B, which is approximately 85 mmHg. Again, the values described herein and are meant to be approximate and merely exemplifying. As such, the values set forth herein are non-limiting. The apparatus 220 or any other apparatus described herein can be configured to provide any suitable or desired level of negative or reduced pressure at any suitable or desired frequency.

As the pump 230 draws air out of the conduits 246, 248 and, hence, increases the level of reduced pressure within the wound dressing 224 from point 2A to point 2B, the air that is drawn out of conduits 246, 248 can be channeled into the air reservoir 260. In other words, the level of positive pressure within the reservoir 260 can be increased while the level of negative pressure in the wound dressing 224 is being increased. Once the level of reduced pressure within the dressing 224 has reached point 2B, the vacuum pump 230 can be stopped and the valve 270 can be closed.

In some embodiments, the vacuum pump 230 can be configured such that air can only flow through the vacuum pump 230 in one direction, to substantially prevent air from flowing from the air reservoir 260 through the vacuum pump 230 into the conduit 236. Additionally, the vacuum pump 230 can be sized and configured to provide as rapid an increase in the reduced pressure as is desired. In some embodiments of the apparatus 220, multiple vacuum pumps or multi-piston pumps 230 can be used to increase the rate of air flow through the apparatus 220, so that the level of reduced pressure within the wound dressing 224 can be cycled at any desired amplitude or frequency.

After the level of reduced pressure within the dressing 224 has reached point 2B, the valve 268 can be switched from the first position to the second position by the control device 232, and the valve 270 can be caused to be closed or remain closed by the control device 232. In some embodiments, the valves 268, 270 can be simultaneously opened and closed, respectively, or the valves 268, 270 can be sequentially opened and closed, respectively. With valve 268 in the second position so that air can flow from the conduit 266 to the conduit 246 but not to conduit 248, and the valve 270 closed, positive pressure or air within the air reservoir 260 can be transferred from the air reservoir 260 to the volume beneath the wound dressing 224, so as to decrease the level of reduced pressure within the dressing from point 2B to point 2C. Once the level of reduced pressure within the volume beneath the wound dressing 224 has reached point 2C, as can be monitored by air pressure sensor 265, the valve 268 can be changed back to the first position so that the level of pressure within the wound dressing 224 is maintained at approximately point 2C.

Thereafter, the level of reduced pressure within the dressing 224 can be maintained at a constant level for a period of time (i.e., from point 2C to point 2D), or it can be approximately immediately increased, such as to the level represented by point 2E. To increase the level of reduced pressure from point 2C or point 2D to point 2E, with the valve 268 in the first position, the valve 270 can be opened, the vacuum pump 230 can again be actuated, and the valve 268 can be opened, causing the vacuum pump to again draw air from the conduits 246, 248 and the volume beneath the wound dressing 224 until the level of pressure within the wound dressing reaches a desired level, such as the level represented by point 2E. When this period elapses, the cycle can repeat as described above. Thus, in this configuration, by circulating the air through the apparatus 220 as described above, the level of reduced pressure within the volume beneath the wound dressing 224 can be rapidly cycled.

Additionally, by reducing the volume within each of the conduits, the volume of the negative pressure airspace that is required to be increased and decreased can be reduced, thus permitting the apparatus 220 to accommodate higher frequencies of sustained variable pressure.

In some embodiments, the apparatus would preferably enable the medical practitioner or patient to set a base level of negative pressure on the wound bed such that there would always be a negative pressure applied to the wound. Although the apparatus is not limited to the specific negative pressure ranges described herein, the following are some of the typical negative pressure ranges that may beneficially promote wound healing or provide other benefits related to negative pressure wound therapy and may be used to define either the base level of negative pressure, or the maximum level of negative pressure, that maybe applied to the wound. For example, in some embodiments the apparatus may be configured so as to provide, and so that the dressing can accommodate, up to approximately 200 mmHg of negative pressure below atmospheric level. In some embodiments, the dressing and other components of the apparatus can be configured to provide greater than approximately 200 mmHg to the wound site, although this level of negative pressure may exceed the generally desired range for many patients. For some embodiments of the apparatus, it may be desired to provide in excess of 200 mmHg of negative pressure to a dressing for purposes of examining a dressing, tubing, pump system, or other components of the apparatus for leaks or other performance-based deficiencies or characteristics.

In some embodiments, the apparatus including the dressing can be configured to provide as little as approximately 15-80 mmHg of negative pressure to the wound. This level of negative pressure, i.e., approximately 15-80 mmHg, is typically associated with greater patient comfort and compliance. Additionally, some embodiments of the apparatus and dressing can be configured to provide and sustain less than approximately 15 mmHg at the wound site, although many wounds that are treated with the apparatus would benefit from a greater level of reduced pressure. Some embodiments of the apparatus can be configured to provide negative pressure levels in excess of approximately 80 mmHg, such as levels up to approximately 150 mmHg.

As mentioned above, the apparatus is preferably configured to provide a pulsed or varying pressure to the wound. The pump would preferably provide the pressure through the tubing to the dressing and the wound. In some embodiments, the apparatus may be configured to allow the medical practitioner or patient to vary either the amplitude or the frequency, or both, of the pulsed or varying pressure to the wound. As mentioned above, the amplitude of the negative pressure can vary between any of the values in any of the ranges described above. In some embodiments, the amplitude of the varying pressure preferably varies between two values of negative pressure such that negative pressure is always provided to the wound. In one non-limiting example, the pump could be configured to maintain a minimum level of negative pressure at, for example, approximately 30 mmHg, and cycle the negative pressure up to a higher level of negative pressure, such as up to approximately 80 mmHg. In this example, the pump would preferably be configured to cycle the negative pressure back down to approximately 30 mmHg, whether through a release of pressure through a port or valve in the apparatus or dressing, or merely by turning off the suction source and allowing inherent leaks in the dressing drop the pressure down.

As mentioned, in some embodiments, the apparatus may be configured to allow a medical practitioner or patient to control or vary the frequency of the cycling between the high and low pressure values. In one non-limiting example, the frequency of the cycling could range from a cycle every approximately 5-10 minutes to a more rapid cycle of approximately 180 cycles per minute. This cycling aspect may allow for faster healing of the wound by stimulating the blood flow.

In some embodiments, the apparatus can comprise sensors such as, but not limited to, temperature, pressure, blood flow, pulse, cardiac cycle, or blood oxygen saturation sensors. Further, in some embodiments, the sensors can be used to automatically trigger the control device to change the magnitude or frequency of the pressure cycling based on the data received from the sensors and pre-programmed algorithms in the control unit used to control the vacuum pump. Accordingly, in some embodiments, when the blood flow rate determined by the blood flow sensor exceeds an optimal or predetermined value, the apparatus can be configured so that the amplitude of negative pressure is decreased. Further, in some embodiments, when the blood oxygen saturation level determined by the blood oxygen saturation sensor falls below an optimal or predetermined value, the apparatus can be configured so that the amplitude of the negative pressure is increased, so as to increase blood flow to the wound.

The sensors can be connected to the control device via leads. The leads are preferably cables or wires constructed of an electrically conductive material, optical fiber, or other suitable medium arranged to enable data transmission from the sensors to the control device, alarm, recording device, and/or a visual display (not shown). The leads can be sealably routed under the wound dressing in a manner that is similar to that for the tubing so as to maintain the gas and fluid impermeable nature of the seal of the wound dressing to the body. In some embodiments, sensors can transmit information wirelessly so that the leads are not needed.

The sensors and leads are preferably sized and configured so as to not irritate or otherwise damage any of the tissue in or around the wound bed when the wound dressing is changed from the semi-rigid configuration to the collapsed configuration. In some configurations, the sensors and leads may be covered with a cotton gauze or other suitable material that will not affect the sensors ability to collect the desired information from the wound bed, but that will protect the wound bed from any damage that may occur if the sensors or the leads contact the wound bed.

In some embodiments, sensors for surface application (for example, for application to the dermis or wound bed) can be used. In some embodiments, sensors that are implantable in the body or otherwise invasively applied can be used. In particular, in some embodiments, the sensors can be positioned inside of the wound dressing so as to be positioned between the wound dressing and the wound. In some embodiments, the sensors can be positioned at least partially within the wound dressing or, in some embodiments, positioned outside of the wound dressing preferably on the surface of or implanted within the healthy skin adjacent to the wound. In some embodiments, the sensors may be positioned in the wound bed. In some embodiments, only one sensor may be positioned in the wound bed. Any sensor presently known in the art that can be used to measure the parameters disclosed herein or other parameters of interest may be used with any of the embodiments of the apparatus or wound dressing disclosed herein.

Figure 5:
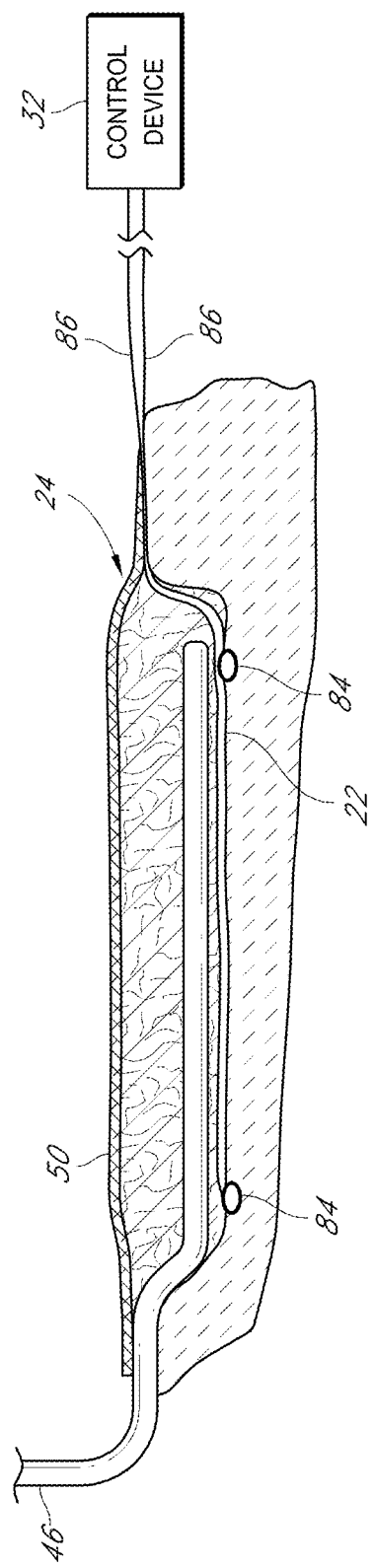
FIG. 5 is a schematic representation of another embodiment of a sustained variable negative pressure wound treatment apparatus, illustrating sensors embedded in the wound.

FIG. 5 is a schematic representation of a portion of a sustained variable negative pressure wound therapy apparatus 20 in which a pair of sensors 84 connected to a control device 32 via leads 86 can be positioned in the wound bed 22. As described above, the wound dressing 24 comprises a fluid-impermeable wound cover 50 and can be secured to the healthy skin surrounding the wound with adhesive (not shown) or by any other suitable method. Either of the sensors illustrated in FIG. 5 can be a temperature, pressure, blood flow, pulse, cardiac cycle, or blood oxygen saturation level sensor, or other any other suitable sensor currently available or later developed. As illustrated in FIG. 5, the sensors 84 can be connected to the control device 32 via leads 86. The leads 86 are preferably cables or wires constructed of an electrically conductive material, optical fiber, or other suitable medium arranged to enable data transmission from the sensors 84 to the control device 32 and alarm device, recording device, and/or a visual display (not shown). The leads 86 can be sealably routed under the wound dressing 24 in a manner that is similar to that for the tubing 46 so as to maintain the gas and fluid impermeable nature of the seal of the wound dressing 24 to the body.

Figure 6:
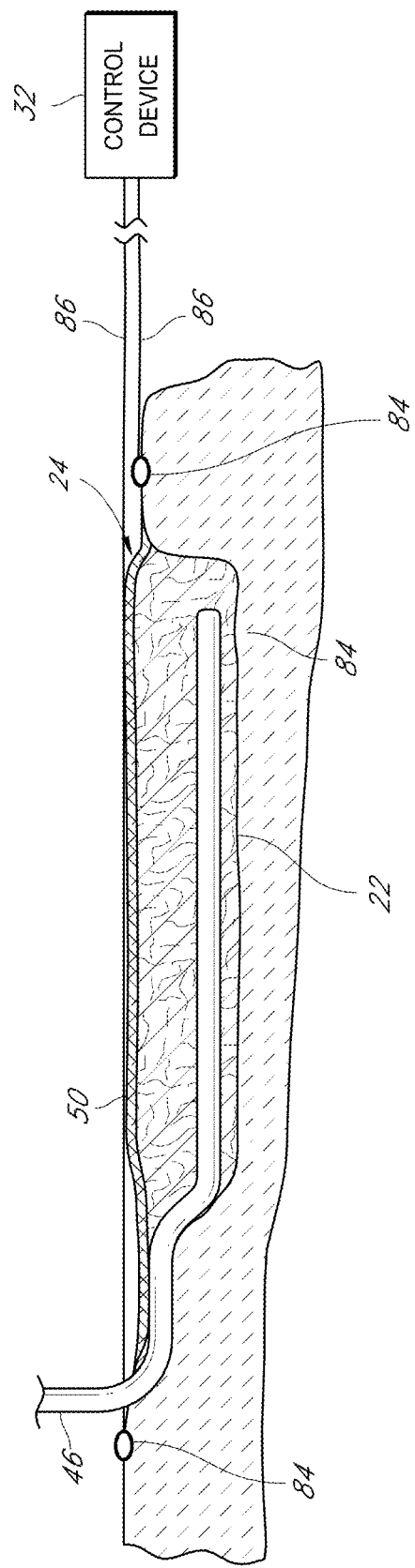
FIG. 6 is a schematic representation of another embodiment of a sustained negative pressure wound treatment apparatus, illustrating sensors positioned adjacent to the dressing.
Figure 7B:
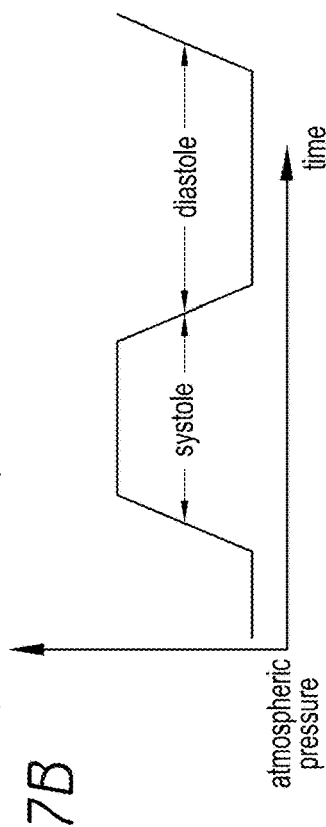
FIG. 7A-7G is a schematic representation of a sustained variable negative pressure program wherein negative pressure cycling is synchronized to a patient's heartbeat.
Figure 7D:
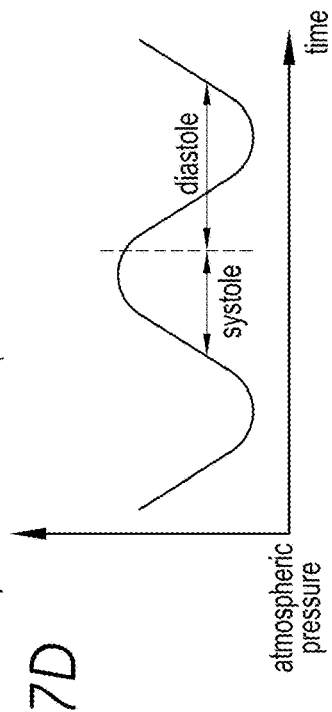
Figure 7A:
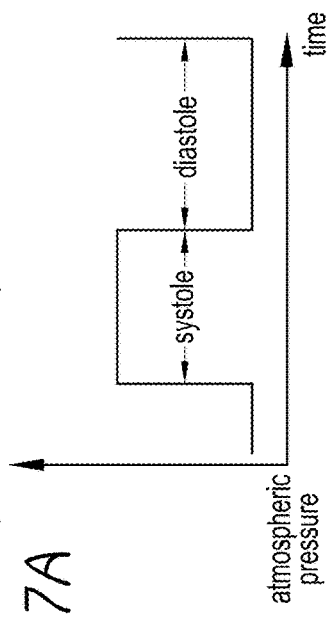
Figure 7C:
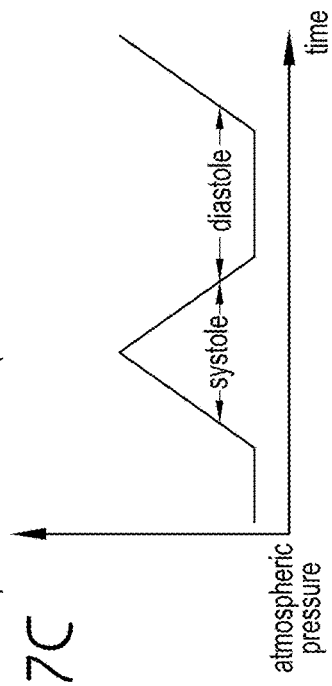
Figure 7E:
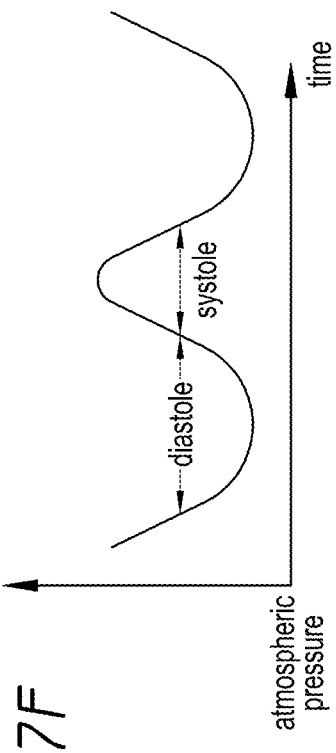
Figure 7F:
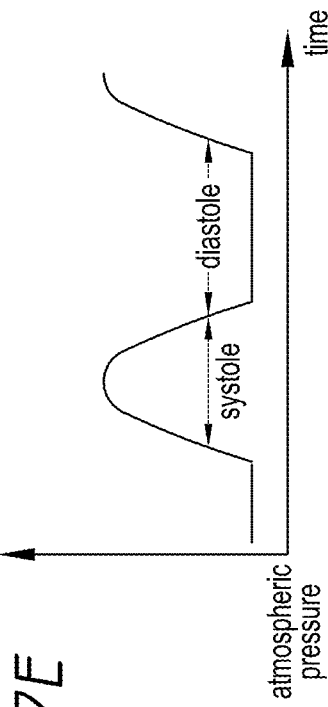
Figure 7G:
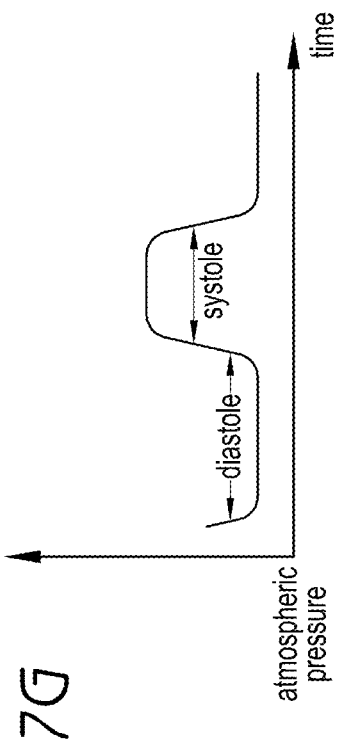

In some embodiments, one or more sensors can be positioned outside of or adjacent to the dressing. FIG. 6 is a schematic representation of a portion of a sustained variable negative pressure wound therapy apparatus 20 in which a pair of sensors 84 connected to a control device 32 via leads 86 can be positioned adjacent to the dressing 24. Either of the sensors illustrated in FIG. 6 can be a temperature, pressure, blood flow, pulse, cardiac cycle, or blood oxygen saturation level sensor, or other any other suitable sensor currently available or later developed. As illustrated in FIG. 6, the sensors 84 can be connected to the control device 32 via leads 86. The leads 86 are preferably cables or wires constructed of an electrically conductive material, optical fiber, or other suitable medium arranged to enable data transmission from the sensors 84 to the control device 32 and alarm device, recording device, and/or a visual display (not shown). The leads can be routed over the wound dressing 24 as is shown, and can be attached to the dressing. The leads can be sealably routed under the wound dressing 24 in a manner that is similar to that for the tubing 46 as to maintain the gas and fluid impermeable nature of the seal of the wound dressing 24 to the body. The leads can also be routed through the tubing 46.

In some embodiments, the apparatus may be configured such that the frequency of the cycling between two or more magnitudes of negative pressure or positive and negative pressure would be synchronized with the patient's heartbeat or cardiac cycle. Sensors configured to measure the patient's heartbeat or cardiac cycle at or near the site of the wound or anywhere on the patient's body may be used to enable the synchronization. Synchronizing the magnitude of the negative pressure to the patient's heartbeat or cardiac cycle may allow better blood flow through the wound and assist with healing. For some patients, the frequency of the cycling may be between approximately 50-120 cycles per minute, so as to be in synchronization with the patient's pulse. Negative pressure can be cycled in the range of 15-200 mmHg below atmospheric pressure. In some embodiments, the synchronization of the frequency of the cycling can be performed by modulating the suction source according to the measured patient's heartbeat or cardiac cycle (e.g., an electrical signal).

As mentioned, in some embodiments, a patient's pulse could be determined with a pulse sensor, which may be attached to the inside of the dressing, otherwise supported by the dressing, or otherwise positioned in the wound bed. In some embodiments, the pulse sensor could be positioned adjacent to the wound site. In some embodiments, the pulse sensor could be positioned at another location on the patient's body preferably close enough to the wound site so as to provide an accurate reading of the patient's pulse at the wound site. Any sensor presently known in the art or later developed can be used to measure the patient's pulse may be used with any of the embodiments of the sustained variable negative pressure wound therapy apparatus or wound dressing disclosed herein. Such sensors may include, but are not limited to, invasive or non-invasive pulse sensors such as pressure transducers, electrodes, photoplethysmographs, and oximeters (e.g., NONIN MEDICAL Pulse Oximeters, www.nonin.com). The patient's pulse can be measured in or adjacent to the wound site, or anywhere on the body. When another device, such as a pacemaker, implantable cardioverter defibrillator (ICD), pulse oximeter, or the like, measures the patient's pulse, the information can be transmitted via leads or wirelessly to the apparatus.

FIG. 7 illustrates application of negative pressure to the wound site by cycling negative pressure synchronized to the patient's cardiac cycle. Each plot illustrates applying greater magnitude of negative pressure during the systolic period, and decreasing the magnitude of negative pressure during the diastolic period. The plots illustrate application of a square (FIG. 7A), half-wave rectified trapezoid (FIG. 7B), and triangular (FIG. 7C) waveforms and symmetric (FIG. 7D), half-wave rectified (FIG. 7E), asymmetric (FIG. 7F), and partially rectified asymmetric (FIG. 7G) sinusoidal waveforms. In some embodiments as is shown in FIG. 7D, the application of greater magnitude of negative pressure may not occupy the entirety of the systolic period, and negative pressure may be released during a portion of the systolic period. In order to improve the blood flow to the capillaries, in some embodiments, it may be advantageous to apply greater magnitude of negative pressure during the diastolic period, and to decrease the magnitude of negative pressure during the systolic period (i.e., reflect the plots of FIG. 7 around the x-axis). Application of negative pressure in synchrony with the patient's cardiac cycle may simulate blood pumping action within the wound site and/or condition the capillaries and other blood vessels to open and close at a faster than normal rate to allow for better blood flow through the wound.

In some embodiments, the apparatus may comprise a pump that allows for increased blood flow by decreasing the constant pressure on the wound below capillary closing pressure. Capillary closing pressure is the pressure that causes blood flow through a capillary to stop. By decreasing the constant pressure below this range, a higher level of blood flow through the capillaries may be maintained. Then the pulsation with increased amplitude may be applied, drawing this increased blood flow into the wound itself.

Blood flow sensors configured to measure the blood perfusion through the wound may be used to deliver negative pressure below capillary closing pressure. Any sensor presently known in the art or later developed that can be used to measure the flow of blood or the perfusion of red blood cells into or adjacent to the wound site may be used with any of the embodiments of the apparatus or wound dressing disclosed herein. Such sensors may include, but are not limited to, the OxyFlo2000, the OxyFlo4000, OxyLab LDF laser Doppler tissue blood perfusion monitors, or laser Doppler blood flow probes developed by Discovery Technology International, Inc. (www.discovtech.com/PAGE1.htm), any of which may be suitable for use with any of the embodiments of the apparatus or wound dressing. Ultrasonic blood flow measurement devices which, in some cases, are based on the laser Doppler technology may also be used to measure the flow of blood. Capillary laser Doppler devices that are implanted within the wound site or adjacent to the wound site may provide the most accurate readings of blood flow or the perfusion of red blood cells into or adjacent to the wound site.

In one non-limiting example, the apparatus may be configured to provide a baseline negative pressure of approximately 10-12 mmHg below atmospheric pressure, and to cycle the negative pressure by increasing the negative pressure applied to the wound by approximately 20-150 mmHg, at a frequency of approximately 20-60 cycles per minute. This is illustrated in FIG. 2, where the baseline negative pressure at about 10 mmHg below atmospheric pressure is applied to the wound. Subsequently, the negative pressure is increased to 85 mmHg below atmospheric pressure for a short duration, and then released back to the baseline negative pressure. The cycle is repeated at a frequency between 20-60 cycles per minute. In another non-limiting example, to provide brief sustained levels of greater negative pressure, the apparatus may be configured for a baseline negative pressure of approximately 20 mmHg below atmospheric pressure, and for cycling the negative pressure by increasing it to approximately 200 mmHg below atmospheric pressure, at a frequency of approximately 120 cycles per minute.

Figure 8:
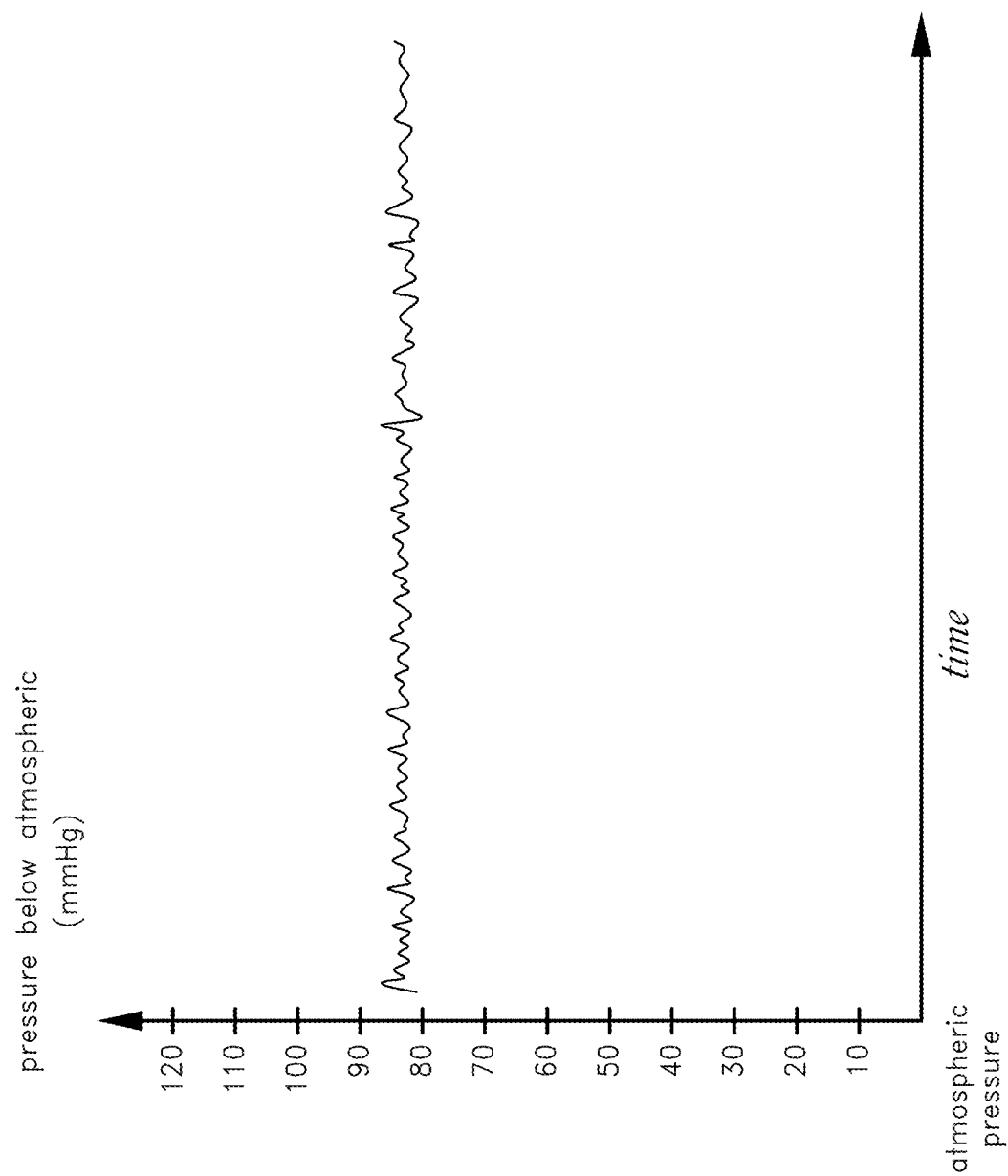
FIG. 8 is a schematic representation of a sustained variable negative pressure program wherein negative pressure cycling comprises pulsing.

In some embodiments, the apparatus may be configured to provide a baseline negative pressure of approximately 5-60 mmHg below atmospheric pressure, and to cycle the negative pressure by increasing the negative pressure applied to the wound by approximately 5-85 mmHg, at a frequency of approximately 200-400 cycles per minute. This high frequency level may be referred to as micro pulsation. Micro pulsation may condition the capillaries and other blood vessels to open and close at a faster than normal rate to allow for better blood flow through the wound. For example, FIG. 8 illustrates micro pulsation around a baseline of approximately 85 mmHg below atmospheric pressure. The negative pressure applied to the wound is increased by approximately 5 mmHg below at a frequency between 200-400 cycles per minute.

In another non-limiting example, the apparatus may be configured to provide a baseline negative pressure of approximately 120 mmHg below atmospheric pressure, and to cycle the negative pressure to a value in the range of approximately 10-20 mmHg, at a frequency of approximately 10-200 cycles per minute, or even slower at approximately 1-2 cycles in five minutes or, even slower, at approximately 1-2 cycles per day.

Because it is believed that optimal values of the magnitude and frequency are highly dependent on the patient, in some embodiments, the apparatus may be configured so that the medical practitioner or patient can adjust the magnitude of the negative pressure and/or the frequency of the cycling. Thus, in some embodiments, the pump would preferably have controls that would enable the amplitude cycling time and duration to be programmed or adjusted.

In some embodiments, the pump would additionally preferably have memory capacity so as to record data that is provided by any of the sensors in the apparatus or so as to store programs that control the cycling nature of the negative pressure. For example, in some embodiments, the pump would preferably have the ability to sense the oxygen levels, blood temperature, pulse, cardiac cycle, or blood flow rate of the wound through a variety of sensors. The pump would then preferably be able to cycle through the various typical or non-typical programs that allow for sustained variable pressure to the wound bed and determine which may be the most optimal for the patient's circumstances and then apply the most optimal program to the wound.

It is also highly likely that the body may adapt or that the wound at some time in the future might need another type of program to optimize the wound healing process. To account for this, in some embodiments, the pump would preferably have the ability to cycle through the typical programs and determine the most optimal program based on oxygen levels, blood temperature, or blood flow rate into the wound, although other parameters could also be used to determine the most optimal negative pressure program.

As mentioned, the apparatus may comprise a control device, an alarm device, and/or other recording device. In some embodiments, however, the apparatus may comprise only the control device. The control device preferably receives signals from the sensors and converts the signals to an electronic or other suitable form that can be recognized by the alarm device. Accordingly, neither the alarm device nor the recording device is required in some arrangements of the apparatus. The alarm device and the recording device are supplemental components that may be added to the apparatus to warn the user or practitioner when the values determined by the sensors exceed predetermined values associated with the sensors, and to record the values transmitted from the sensors over a predetermined amount of time, respectively. As such, any of the embodiments of the apparatus described herein can operate without the addition of the alarm device and/or recording device.

With reference to FIG. 9, the apparatus 20 may comprise a control device 32, an alarm device 88, and/or other recording device 90. The alarm device 88 may produce any type of audible sound when activated, such as a ringing sound, buzzing, chirping or any other common alarm noise. Alternatively, the alarm device 88 may include a digitally produced audible voice that presents pre-arranged messages corresponding to different conditions in the area of the wound site 22. The alarm device 88 preferably produces different levels of the alarm depending upon the magnitude of the measurements received from the sensors 84. For example, if the blood flow rate, pulse, cardiac activity, or temperature drops below or rises above predetermined values, as measured by the sensors 84, the alarm device 88 may sound successive alarm pitches, sounds, messages or series of sounds. Similarly, as the blood oxygen saturation level measured by any of the one or more sensors 84 falls below or rises above a predetermined value, the apparatus 20 may be configured to alert the user. As mentioned above, the control device 32 may also control the vacuum pump 30 to adjust the negative pressure under the wound dressing 24, and the negative pressure under the wound dressing 24 may be adjusted in response to the data collected by the sensors 84.

The recording device 90 may be any device designed to record data received from the sensors 84. Such devices are preferably capable of recording data on compact disks, DVD disks, floppy disks, magnetic tape, integrated circuits, or other similar media in digital form. Alternatively, the recording device 90 can be a "manual" device that records or displays data through a chart recorder or visual electronic display, such as an LCD or CRT monitor. Such information can be in the form of real-time data, or an average over a predetermined duration of time, or any other suitable form. In some embodiments, information regarding the pulse level could be displayed as follows: (i) Pulse Steady; (ii) Pulse Increasing; or (iii) or Pulse Decreasing. In some embodiments information regarding blood flow could be displayed as follows: (i) Blood Flow Steady; (ii) Blood Flow Increasing; or (iii) or Blood Flow Decreasing. Thus, the apparatus 20 or display could embody this information that is being gathered by one or more of the sensors 84 to help with the wound healing as well as provide important information to a health care practitioner studying the effects of such parameters on wound healing.

While the above detailed description has shown, described, and pointed out novel features as applied to various embodiments, it will be understood that various omissions, substitutions, and changes in the form and details of the device or process illustrated may be made without departing from the spirit of the disclosure. Additionally, the various features and processes described above may be used independently of one another, or may be combined in various ways. All possible combinations and subcombinations are intended to fall within the scope of this disclosure.

As will be recognized, certain embodiments described herein may be embodied within a form that does not provide all of the features and benefits set forth herein, as some features may be used or practiced separately from others. The scope of the inventions is indicated by the appended claims rather than by the foregoing description. All changes which come within the meaning and range of equivalency of the claims are to be embraced within their scope.

What is claimed is:

1. A method of operating a negative pressure wound therapy apparatus, the method comprising:

applying, via a fluid flow path, reduced pressure from a suction source to a wound dressing placed over a wound;

monitoring a temperature at the wound using a sensor positioned at least partly in the wound or the wound dressing or positioned adjacent to the wound dressing; and adjusting the reduced pressure from the suction source by cycling the reduced pressure from the suction source between two different negative pressure values according at least to the temperature at the wound.

2. The method of claim 1, wherein said adjusting comprises adjusting a frequency of the reduced pressure from the suction source according at least to the temperature at the wound.

3. The method of claim 1, wherein said adjusting comprises adjusting the reduced pressure from the suction source in response to determining that the temperature at the wound satisfies a threshold.

4. The method of claim 1, wherein said adjusting comprises adjusting the reduced pressure from the suction source further according to a user input.

5. The method of claim 1, wherein said cycling comprises cycling the reduced pressure from the suction source in a sinusoidal pattern.

6. The method of claim 1, further comprising receiving a sensor signal from the sensor via leads that are routed under the wound dressing, and wherein said monitoring comprises monitoring the temperature at the wound using the sensor signal from the senor.

7. The method of claim 1, further comprising wirelessly receiving a sensor signal from the sensor, and wherein said monitoring comprises monitoring the temperature at the wound using the sensor signal from the senor.

8. The method of claim 1, further comprising activating an alarm according at least to the temperature at the wound.

9. The method of claim 1, wherein the sensor comprises a plurality of sensors.

10. The method of claim 1, wherein the reduced pressure from the suction source is below atmospheric pressure.

11. The method of claim 1, wherein the sensor is positioned at least partly in the wound dressing.

* * * * *

UNITED STATES PATENT AND TRADEMARK OFFICE
CERTIFICATE OF CORRECTION

PATENT NO. : 10,493,182 B2
APPLICATION NO. : 16/009699
DATED : December 3, 2019
INVENTOR(S) : Weston et al.

Page 1 of 1

It is certified that error appears in the above-identified patent and that said Letters Patent is hereby corrected as shown below:

On the Title Page

On Page 4, Column 1, Item (56), Line 4, under Other Publications, delete "Wunddrainage" insert --Wounddrainage--.

In the Specification

In Column 5, Line 11 (approx.), delete "FIG." and insert --FIGS.--.

In Column 6, Line 8, delete "can by" and insert --can be--.

In the Claims

In Column 24, Line 29, Claim 6, delete "senor" and insert --sensor--.

In Column 24, Line 33, Claim 7, delete "senor" and insert --sensor--.

Signed and Sealed this
Twenty-fifth Day of February, 2020

Andrei Iancu
*Director of the United States Patent and Trademark Office*